United States Patent [19]
Rokita et al.

[11] Patent Number: 5,831,073
[45] Date of Patent: *Nov. 3, 1998

[54] ION TRIGGERED ALKYLATION OF BIOLOGICAL TARGETS BY SILYLOXY AROMATIC AGENTS

[75] Inventors: Steven E. Rokita, Silver Spring, Md.; Tianhu Li, San Diego, Calif.; Qingping Zeng, Austin, Tex.

[73] Assignee: The Research Foundation of State University of New York, Albany, N.Y.

[*] Notice: The term of this patent shall not extend beyond the expiration date of Pat. No. 5,296,350.

[21] Appl. No.: 603,221

[22] Filed: Feb. 20, 1996

Related U.S. Application Data

[63] Continuation-in-part of Ser. No. 71,116, Jun. 2, 1993, Pat. No. 5,493,012, which is a continuation-in-part of Ser. No. 606,463, Oct. 31, 1990, Pat. No. 5,296,350.

[51] Int. Cl.$^6$ .................................................. C07H 19/04
[52] U.S. Cl. ........................... 536/26.6; 536/23.1; 556/9; 514/44
[58] Field of Search .................................. 536/26.6, 23.1; 435/6, 91, 91.2; 556/9; 514/44

[56] References Cited

U.S. PATENT DOCUMENTS

| 5,292,873 | 3/1994 | Rokita et al. | 536/24.3 |
| 5,493,012 | 3/1994 | Rokita et al. | 536/26.6 |

FOREIGN PATENT DOCUMENTS

PCT/WO85/02628 6/1985 WIPO.

OTHER PUBLICATIONS

Landegren et al., "DNA Diagnostics–Molecular Techniques and Automation", Science, 242, 229 (1988).
Miller et al., "Oligonucleotide Inhibitors of Gene Expression in Living Cells: New Opportunities in Drug Design", Ann. Reports in Med. Chem., 23, 295 (1988).
Toulme et al., "Antimessenger Oligodeoxyribonucleotides: An Alternative to Antisense RNA for Artificial Regulation of Gene Expression—A Review", Gene, 72, 51–58 (1988).
Stein et al., "Oligodeoxyribonucleotides as Inhibitors of Gene Expression: A Review", Cancer Research, 48, 26592668 (1988).
Barton, "Metals and DNA: Molecular Left–Handed Complements", Science, 233, 727–734 (1986).
Blake et al., "Hybridization Arrest of Globin Synthesis in Rabbit Reticulocyte Lysates and Cells by Oligodeoxyribonucleoside Methylphosphonates", Biochemistry, 24, 6139–6145 (1985).
Agrawal et al., "Oligodeoxynucleoside Phosphoramidates and Phosphorothioates as Inhibitors of Human Immunodeficiency Virus", Proc. Natl. Acad. Sci. USA, 85, 7079–7083 (1988).
Iverson et al.,, "Nonenzymatic Sequence–Specific Cleavage of Single–Stranded DNA to Nucleotide Resolution. DNA Methyl Thiolether Probes", J. Am. Chem. Soc., 109, 12411243 (1987).
Maher III et al., "Inhibition of DNA Binding Proteins by Oligonucleotide–Directed Griple Helix Formation", Science, 245, 725–730 (1989).
Griffin et al., "Recognition of Thymine–Adenine Base Pairs by Guanine in a Pyrimidine Triple Helix Motif", Science, 245, 967–971 (1989).
Strobel et al., "Site–Specific Cleavage of a Yeast Chromosome by Oligonucleotide–Directed Triple–Helix Formation", Science, 249, 73–75 (1990).
Symons, Nucleic Acid Probes, CRC Press, Inc., Boca Raton, Florida (1989).
Gamper et al., "Reverse Southern Hybridization", Nucl. Acids Res., 14, 9943 (1986).
Knorre et al., "Complementary–Addressed (Sequence Specific) Modification of Nucleic Acids", Prog. Nucleic Acids Res. Mol. Biol., 32, 291 (1985).
Knorre, et al., "Complementary–Addressed (Sequence Specific) Modification of Nucleic Acids", Prog. Nucleic Acids Res. Mol. Biol., 32, 291 (1985).
Meyer et al., "Efficient, Specific Crosslinking and Cleavage of DNA by Stable, Synthetic complementary oligonucleotides", J. Am. Chem. Soc., 111, 8517 (1989).
Van Houten et al., "Action Mechanism of ABC Excision Nuclease on a DNA Substrate Containing a Psoralen Crosslink at a Defined Position", Proc. Natl. Acad. Sci. USA, 83, 8077 (1986).
Lee et al., "Interaction of Psoralen–Derivatized Oligodeoxyribonucleoside Methylphosphonates with Single–Stranded DNA", Biochemistry, 27, 3197–3203 (1988).
Chatterjee et al., "Inducible Alkylation of DNA Using an Oligonucleotide Quinone Conjugate", J. Am. Chem. Soc., 112, 6397 (1990).

(List continued on next page.)

*Primary Examiner*—Scott W. Houtteman
*Attorney, Agent, or Firm*—Hoffmann & Baron, LLP

[57] ABSTRACT

A silyloxy aromatic derivative capable of alkylating a target biological molecule when activated by ionic strength. A sequence directed reagent may be constructed by conjugating a methyl silyloxy aromatic derivative to a hexamethylamino linker attached to either the 5' or 3' terminus of an oligonucleotide. Annealing this modified fragment of DNA to its complementary sequence allows for target modification subsequent to ionic activation. The product of this reaction is a covalent crosslink between the reagent and target strands resulting from an alkylation of DNA by the activated silyloxy aromatic derivative. In a preferred embodiment, a nitrophenyl or bromo group is attached to a methyl group of the silyloxy aromatic derivative. This reagent may be similarly linked to an oligonucleotide probe. Activation of the alkylating agent by an ionic signal (X) which may naturally occur, or may be introduced into the media containing the target molecule, such as by the introduction of a salt (MX).

30 Claims, 8 Drawing Sheets

OTHER PUBLICATIONS

Ramage et al., "Solid Phase Peptide Synthesis: Fluoride Ion Release of Peptide from the Resin", Tet. Lett., 28, 4105–4108 (1987).

Mullen et al., "A New Fluoridolyzable Anchoring Linkage for Orthogonal Solid Phase Peptide Synthesis", J. Org. Chem., 53, 5240 (1988).

Trahanovsky et al., "Observation of Reactive o–Quinodimethanes by Flow NMR", J. Am. Chem. Soc., 110, 6579 (1988).

Angle et al., "p–Quinone Methide Initiated Cyclization Reactions", J. Am. Chem. Soc., 111, 1136 (1989).

Wahl et al., "Northern and Southern Blots", Meth. Enzymol., 152, 572–573 (1987).

Higuchi et al., "DNA Typing from Single Hairs", Nature, 332, 543–546 (1988).

Conner et al., "Detection of Sickle Cell 4'–Globin Allele by Hybridization with Synthetic Oligonucleotides", Proc. Natl. Acad. Sci. USA, 80, 278–282 (1983).

Jager et al., "Oligonucleotide N–Alkyl–phosphotamides: Synthesis and Binding to Polynucleotides", Biochemistry, 27, 7237–7246 (1988).

Cocuzza, "Total synthesis of 7–Iodo–2', 3'–Dideoxy–7–Deazpurine Nucleosides, Key Intermediates in the Preparation of Reagents for the Automated Sequencing of DNA", Tet. Lett., 29, 4061–4064 (1988).

Hanna et al., "Synthesis and Characterization of 5–[(4Azidophenacyl)thio]uridine 5' Triphosphate, a Cleavable Photo–Cross Linking Nucleotide Analogue", Biochemistry, 28, 5814–5820 (1989).

Gibson et al., "Synthesis and Application of Derivatizable Oligonucleotides", Nucl. Acids Res., 15, 6455–6467 (1987).

Nelson et al., "A New and Versatile Reagent for Incorporating Multiple Primary Aliphatic Amines Into Synthetic Oligonucleotides", Nucl. Acids Res., 17, 71797186 (1989).

Maniatis et al., Molecular Cloning. A Laboratory Manual, Cold Spring Harbor Laboratory, Cold Spring Harbor, NY (1982).

Raval et al., J. Univ. Bombay, 7. Pt. 3, 184–188 (1938); CA 33, 3779 (1939).

Ramage et al., Tet. Lett., 28, 4105–4108 (1987).

Dreyer et al., Proc. Natl. Acad. Sci. USA, 82, 968–972 (1985).

Chu et al., Proc. Natl. Acad. Sci. USA, 82, 963–967 (1985).

Mack et a., J. Am. Chem. Soc., 110, 7572–7574 (1988).

Remers, "Antineoplastic Agents", Ch. 8, Wilson and Gisvold's Textbook of Organic Medicinal and Pharmaceutical Chemistry, 9th Ed., Delgado et al., eds., 313–353, J.B. Lippincott co.' Philadelphia ( ).

Goodchild, "Conjugates of Oligonucleotides and Modified Oligonucleotides: A Review of Their Synthesis and Properties", Bioconjugate Chem., 1, 165–187 (1990).

Uhlmann et al., "Antisense Oligonucleotides: A New Therapeutic Principle", Chem. Rev., 90, 543–584 (1990).

Nielsen, "Sequence–Selective DNA Recognition by Synthetic Ligands", Bioconjugate Chem., 2, 1–12, (1991).

Englisch et al., "Chemically Modified Oligonucleotides as Probes and Inhibitors", Angew. Chem Int. Ed. Engl., 30, 613–629 (1991).

Brakel, ea., Discoveries in Antisense Nucleic Acids, Gulf Publishing Co., Houston (1989).

Praseuth et al., "Sequence–Specific Binding and Photocrosslinking of $\alpha$ and $\beta$ Oligodeoxynucleotides to the Major Groove of DNA via Triple–Helix Formation", Proc. Natl. Acad. Sci. USA, 85, 1349–1353 (1988).

FIG-2 FLUORIDE INDUCED ALKYLATION OF DNA

FIG-3 IONIC STRENGTH TRIGGERS SOLVOLYSIS TO FORM THE QUINONE METHIDE

ION TRIGGERED ALKYLATION OF BIOLOGICAL TARGETS BY SILYLOXY AROMATIC AGENTS

This application is a continuation-in-part of application Ser. No. 08/071,116 filed on Jun. 2, 1993, now U.S. Pat. No. 5,493,012, which is a continuation-in-part of application Ser. No. 07/606,463 filed on Oct. 31, 1990, now U.S. Pat. No. 5,296,350.

BACKGROUND OF THE INVENTION

1. Field of the Invention

This invention relates to silyloxy aromatic alkylating agents that optionally include a probe capable of associating with biological targets. The alkylating agents are activated for reaction by ionic strength.

2. Background of the Related Art

Currently prescribed chemotherapeutic agents acting at the level of DNA are often effective, but their therapeutic index is quite poor, limited by the lack of target specificity. An international research effort has been underway using a wide range of techniques to develop a gene specific drug—a "magic bullet" that is aimed at a single DNA sequence within a cell.

The technological advances allowing for facile DNA synthesis have produced innumerable protocols which rely on custom oligonucleotides, used as probes to screen for complementary sequences within plasmids, chromosomes and DNA libraries. See, for example, Landegren et al., "DNA Diagnostics-Molecular Techniques and Automation", *Science*, 242, 229 (1988). The specificity of oligonucleotide hybridization has been utilized for "antisense" methods controlling selective expression of genes both in vivo and in vitro. For example, see Miller et al., "Oligonucleotide Inhibitors of Gene Expression in Living Cells: New opportunities in Drug Design", *Ann. Reports in Med. Chem.*, 23, 295 (1988). Sequence recognition by the binding of probes most often depends on only the non-covalent forces of hydrogen bonding formed between complementary base pairs. Complexation of this type is quite sufficient for many applications, but covalent cross-linking of duplex structures could simplify many of the current protocols and provide new opportunities for processing DNA in a sequence specific manner. Messenger RNA has become a viable target for inhibiting the expression of a desired gene in vivo. See, for example, Toulme et al., "Antimessenger oligodeoxyribo-Nucleotides: An Alternative to Antisense RNA for Artificial Regulation of Gene Expression—A Review", *Gene*, 72, 51–58 (1988); and, Stein et al., "Oligodeoxyribo-Nucleotides as Inhibitors of Gene Expression: A Review", *Cancer Research*, 48, 2659–2668 (1988). Compounds created for this selective reaction have drawn from the advances in site specific modification of DNA. For example, see Barton, "Metals and DNA: Molecular Left-Handed Complements", *Science*, 233, 727–734 (1986), and Dervan, "Design of Sequence-Specific DNA-Binding Molecules", *Science*, 232, 464–471 (1986).

Use of such compounds also depends on the synthesis of metabolically stable oligonucleotides that can traverse cell membranes. For example, see Blake et al., "Hybridization Arrest of Globin Synthesis in Rabbit Reticulocyte Lysates and Cells by Oligodeoxyribonucleoside Methylphosphonates", *Biochemistry*, 24, 6139–6145 (1985). Also, see Agrawal et al., "Oligodeoxynucleoside phosphoramidates and phosphorothioates as inhibitors of human immunodeficiency virus", *Proc. Natl. Acad. Sci. U.S.A.*, 85, 7079–7083 (1988).

Only recently introduced, the technique of oligonucleotide-directed irreversible DNA modification holds great potential as an in vitro tool for molecular biologists. See, for example, Dervan, "Design of Sequence-Specific DNA-Binding Molecules", *Science*, 232, 464–471 (1986); and Iverson et al., in "Nonenzymatic Sequence-Specific Cleavage of Single-Stranded DNA to Nucleotide Resolution. DNA Methyl Thiolether Probes", *J. Am. Chem. Soc.*, 109, 1241–1243 (1987). Site specificity is enforced by the hybridization of the oligomer-reactant to its complement sequence prior to reagent action. Target selectivity can then be conferred, in theory, to most reactive compounds by attaching them to oligonucleotides. The required prehybridization step, however, generally limits this technique's applicability to accessible single strand polynucleotide targets or duplex probes when triple helical formation is possible, see Maher III et al., "Inhibition of DNA Binding Proteins by Oligonucleotide-Directed Triple Helix Formation", *Science*, 245, 725–730 (1989); *Science* 245, 967–971 (1989); and *Science*, 249, 73–75 (1990).

Site-directed covalent modification is also constrained by the nature of the reactive group incorporated into the oligomer. Although a large number of reactive appendages are available for related use in vitro, as reported by Iverson et al., *J. Am. Chem. Soc.*, 109 (1987) supra; and by Dervan, *Science*, 232 (1986) supra, only a limited set of these may apply in a controlled activated manner, either in vitro or for in vivo use.

Sequence recognition between synthetic oligonucleotides and macromolecular DNA represent the keystone of numerous techniques required in molecular biology. For example, see Symons, *Nucleic Acid Probes*, CRC Press, Inc., Boca Raton, Fla. (1989). The fidelity of this process is typically determined only by the hydrogen bonds formed between complementary bases of double and triple helical DNA. Such associations are sufficient for most applications, but covalent stabilization of a target-probe complex could simplify a variety of protocols including those used to diagnose genetic, malignant and infectious diseases; e.g., see discussions by Landegren et al., "DNA-Diagnostic, Molecular Techniques and Automation", *Science*, 242, 229 (1988); and Gamper et al., "Reverse Southern Hybridization" *Nucleic Acids Research*, 14, 9943 (1986).

A general method for this cross-linking has been demonstrated with the construction of oligonucleotide-directed alkylating agent, reported by Knorre et al., "Complementary-Addressed (Sequence-Specific) Modification of Nucleic Acids", *Prog. Nucleic Acids Res. Mol. Biol.*, 32, 291 (1985); Webb and Matteucci, "Sequence-Specific Crosslinking of Deoxyoligonucleotides via Hybridization-Triggered Alkylation", *J. Am. Chem. Soc.*, 108, 2764 (1986); Dervan, "Design of Sequence-Specific DNA-binding Molecules", *Science*, 232, 464 (1986); and Meyer et al., "Efficient, Specific Crosslinking and Cleavage of DNA by Stable, Synthetic Complementary Oligonucleotides", *J. Am. Chem. Soc.*, 111, 8517 (1989). However, limitations are placed on these reagents because of their inherent reactivity. Only mildly reactive species would allow for target recognition to precede covalent modification. An alternative approach has relied on moieties that remain inert until triggered by a chemical or photochemical signal. For example, see Van Houten et al., "Action Mechanism of ABC Excision Nuclease on a DNA Substrate Containing a Psoralen Crosslink at a Defined Position", *Proc. Natl. Acad. Sci. USA*, 83, 8077 (1986); Lee et al., "Interaction of Psoralen-Derivatized oligodeoxyribo-nucleoside Methylphosphonates with Single-Stranded DNA", *Biochemistry*, 27, 3197

(1988); Iverson et al., "Nonenzymatic Sequence-Specific Cleavage of Single-Stranded DNA to Nucleotide Resolution. DNA Methyl Thiolether Probes", *J. Am. Chem. Soc.*, 109, 1241 (1987); Chatterjee and Rokita, "Inducible Alkylation of DNA Using an Oligonucleotide-Quinone Conjugate" *J. Am. Chem. Soc.* 112, 6397 (1990); and also see co-pending patent application U.S. Ser. No. 07/442,947, filed on Nov. 29, 1989 the disclosure of which is incorporated by reference herein.

Organosilane compounds have been used as intermediates in the formation of quinone methides in aprotic solvents. For example, see Ramage et al., "Solid Phase Peptide Synthesis: Fluoride Ion Release of Peptide from the Resin", *Tet. Lett.*, 28, 4105 (1987); Mullen and Barany, "A New Fluoridolyzable Anchoring Linkage for Orthogonal Solid Phase Peptide Synthesis", *J. Org. Chem.*, 53, 5240 (1988); Trahanovsky et al., "Observation of Reactive o-Quinodimethanes by Flow NMR", *J. Am. Chem. Soc.*, 110, 6579 (1988); and Angle and Turnbull, "p-Quinone Methide Initiated Cyclization Reactions", *J. Am. Chem. Soc.*, 111, 1136 (1989).

Yabusaki et al., in PCT Published Application No. WO85/02628, describe cross-linking agents for binding an oligonucleotide probe to a target DNA or RNA molecule. Three types of cross-linking agents are described, including "bifunctional photoreagents", "mixed chemical and biochemical bifunctional reagents"and "bifunctional chemical cross-linking molecules". The bifunctional photoreagents contain two photochemically reactive sites that bind covalently to the probe and to the target molecules. The mixed chemical and photochemical bifunctional reagent is bound non-photochemically to the probe molecule, followed by photochemical binding to the target molecule. Non-photochemical binding is described as a chemical reaction such as alkylation, condensation or additional. Bi-functional chemical cross-linking molecules are said to be activated either catalytically or by high temperature following hybridization.

Although Yabusaki et al. generally hypothesize the concept of a bifunctional photochemical reagent and a mixed chemical and photochemical reagent, there is no specific description of these molecules. All of the reagents they describe are well known photochemical reagents, these include the psoralen derivatives, including furocoumarins, the benzodipyrone derivatives, and the bis-azide derivatives. None of these molecules, however, work on the basis of ionic activation. These reagents, especially the psoralen derivatives, are toxic, causing severe burning of the organism after exposure to sunlight. Finally, the covalent crosslinks formed by psoralens are not permanent, rather, they are degraded by UV irradiation.

Two recent articles reported the use or psoralen crosslinks of DNA substrates, the first by Van Houten et al., in "Action Mechanism of ABC Excision Nuclease on a DNA Substrate Containing a Psoralen Crosslink at a Defined Position", *Proc. Natl. Acad. Sci. USA*, 83, 8077–8081 (1986), and the second by Lee et al., in "Interaction of Psoralen-Derivatized oligodeoxyribonucleoside Methyl-Phosphonates with Single-Stranded DNA", *Biochemistry*, 27, 3197–3203 (1988). Both articles reported covalent cross-linking between the DNA molecule and a complementary oligomer that contains a psoralen derivative. The covalent binding of the psoralen derivative to the DNA molecule was activated by UV irradiation. Accordingly, just like the Yakusaki patent application, the covalent crosslinks formed by psoralens are not permanent, being degraded by UV irradiation.

The techniques of Northern and Southern blotting are two of the most powerful and frequently used procedures in molecular biology, see Wall et al., "Northern and Southern Blots", *Methods Enz.*, 152, 572–573 (1987). Yet the necessary manipulations are time consuming and are not likely to be automated under current technology. Often the polynucleotide (RNA, DNA) under analysis must first be fractionated by size, transferred onto a solid support and then treated through a series of steps to ensure only specific binding of a probe. Detection of the hybridized products usually depends on radiolabelling, heavy metal derivatization or antibody complexation. The methods of blotting have been a staple of basic research, and now also serve in an ever increasing number of commercial kits used to diagnose genetic, malignant, and infectious diseases. See Landegren et al., "DNA Diagnostics-Molecular Techniques and Automation", *Science*, 242, 229 (1988). Related advances have also allowed these processes to aid in forensic science, see Higuchi et al., "DNA Typing from Single Hairs", *Nature*, 332, 543–546 (1988); and the Human Genome Project, see Conner et al., "Detection of Sickle Cell $\beta^3$-Globin Allele by Hybridization with Synthetic Oligonucleotides", *Proc. Natl. Acad. Sci. USA*, 80, 278–282 (1983).

Psoralens have been used to randomly crosslink duplex DNA during hybridization in order to facilitate Southern Blotting procedures. This new test is referred to as Reverse Southern blotting. For example, see Gamper et al., "Reverse Southern Hybridization", *Nucl. Acids Res.*, 14, 9943 (1986). Other biochemical and reduction activated reagents are needed to replace or complement psoralens for sequence detection and to provide an alternate set of conditions for duplex stabilization.

Accordingly, none of the related art describes or suggests using ionic activation with aromatic silyloxy alkylating agents in order to permanently alkylate a biological molecule such as DNA.

Therefore, it is a purpose of the present invention to provide a new class of ionically activated alkylating probes which form a permanent covalent crosslink.

Another purpose of the present invention is to provide an ionically activated alkylating probe which can be used in vivo.

A further goal of the present invention is to provide a new class of ionically activated Reverse Southern blotting reagents for conjugating and permanently crosslinking target oligonucleotides and facilitate blotting procedures, sequence detection and nucleic acid fragmentation.

SUMMARY OF THE INVENTION

These and other purposes and goals are achieved by the present invention which provides a process and alkylating agent for selectively and permanently alkylating a target molecule. The process includes a step of providing an alkylating agent, namely a silyloxy aromatic derivative, capable of alkylating a target molecule. The silyloxy aromatic compound may non-specifically localize to the target molecule. Alternatively, the process may further include linking the silyloxy aromatic derivative to a probe capable of localizing it to the target molecule. The probe, such as an oligonucleotide, may be capable of recognizing a predetermined binding site on a target molecule, such as a specific sequence of a nucleic acid, which is complementary to the probe.

The preferred silyloxy aromatic compound of the invention comprises a substituted aromatic ring system, to which have been attached a silyloxy moiety ($-OSiR_6R_7R_8$) and, in conjugation with the silyloxy moiety through the ring system, at least one substituted methyl group ($-CR_9R_{10}X$).

In the preferred embodiment $R_6$, $R_7$ and $R_8$ are alkyl or aromatic groups. Most preferably $R_6$ and $R_7$ are methyl groups while $R_8$ is a t-butyl moiety. $R_9$ and $R_{10}$ are H or an alkyl or aromatic group. If more than one —$CR_9R_{10}$ X group occupies a position on the ring system and in conjugation with the silyloxy moiety then the —$CR_9R_{10}$ X moieties need not be identical, with $R_9$, $R_{10}$ and X being selected independently of the $R_9$, $R_{10}$ and X of other —$CR_9R_{10}X$ moieties.

The siloxy aromatic derivatives of the present invention contain at least one substituted aromatic center, such as a substituted benzene ring. If more than one aromatic ring is included, the rings are preferably fused, such as a naphthalene, anthracene, or phenanthrene. One or more rings may optionally be heterocyclic, containing a ring member other than carbon, such as oxygen or nitrogen, while preserving the aromatic character of the ring. Suitable heterocyclic aromatic systems include, for example, quinolines, azanthracenes, and azaphenanthrenes.

The alkylating agent may have the general formula:

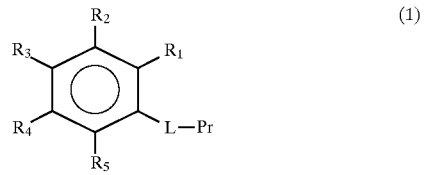

(1)

When
   $R_1$=—$OsiR_6R_7R_8$, then $R_2$ and/or $R_4$ can be=— $CR_9R_{10}X$.
When
   $R_2$=—$OsiR_6R_7R_8$, then $R_1$, $R_3$ and/or $R_5$ can be=— $CR_9R_{10}X$.
When
   $R_3$=—$OsiR_6R_7R_8$, then $R_2$ and/or $R_4$ can be=— $CR_9R_{10}X$.
When
   $R_4$=—$OsiR_6R_7R_8$, then by symmetry $R_4$ is equivalent to R to $R_2$ as described above.
When
   $R_5$=—$OsiR_6R_7R_8$, then by symmetry $R_5$ is equivalent to R as described above.
   $R_6$, $R_7$, $R_8$=various alkyl or aromatic groups;
   X=leaving group, and
Wherein $R_9$ and $R_{10}$ can be H, or an organic derivative, such as an aliphatic or aromatic group. $CR_9R_{10}X$ is positioned on any of the carbon atoms of the ring structure in resonance with the oxygen of the silyloxy moiety; L is a linking group optionally present for attachment to a probe which may be positioned at any carbon atom of the ring, and P is a probe for binding to a target molecule. Preferably, the targeted alkylating agent of the present invention has the general formula:

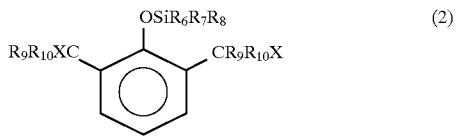

(2)

In this embodiment, an -L-Pr moiety may optionally be present at any of the unoccupied positions of the benzene ring. $R_9$ and $R_{10}$ are independently H, or an organic derivative, such as an aliphatic or aromatic group, and X is a leaving group.

The alkylating agent need not be restricted to a single aromatic ring. For example it may have a multi-ring structure,

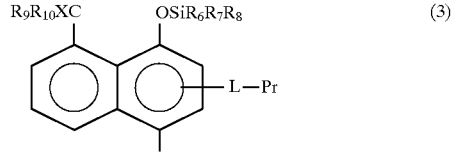

(3)

or,

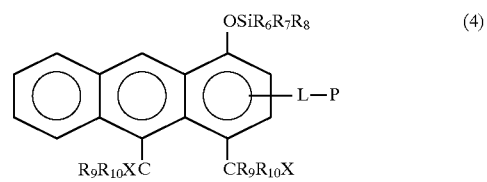

(4)

Alternatively, the alkylating agent may have a ring structure comprising more than one aromatic ring, including one or more heterocyclic aromatic rings, such as acridine, a well known intercalator:

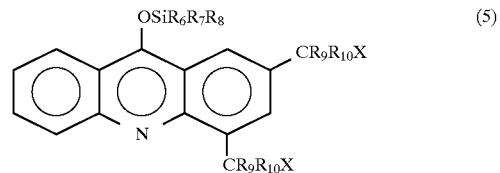

(5)

The alkylating agent, optionally linked to a localizing probe, is then introduced into a system containing the target molecule to allow the alkylating agent and/or the probe to associate, i.e., hybridize, with the target molecule and to thereby localize the silyloxy aromatic derivative near the target molecule. The targeted alkylating agent is activated by ionic strength, which causes covalent bonding between the silyloxy aromatic derivative and the target molecule. If a probe is used, the covalent bonding occurs at a site proximal to the association site of the probe.

In a preferred embodiment, the X group is a displaceable reactive moiety attached to an alkyl group positioned on a carbon atom of the silyloxy aromatic ring. Examples of such groups include Br, Cl, F, I, —OAc, —OH, —$OSO_2CH_3$, —$OSO_2C_6H_4CH_3$—p, —$OCH_2CH_3$, —$OCONHCH_3$, —$OCONHCH_2CH_2R$, —$OC_6H_4NO_2$, —$OC_6H_5$, and —$SC_6H_5$. The alkylating agent is activated, in vitro by adjusting ionic strength, and in vivo by naturally occurring ionic strength. The ionic strength of the in vitro environment capable of activating the alkylating agent is between about 1 mM and about 10M, prafarably between about 100 mM and about 2M.

For a better understanding of the present invention reference is made to the following description made in conjunction with the figures, the scope of which is defined in the claims.

DETAILED DESCRIPTION OF THE INVENTION

Figure 1:
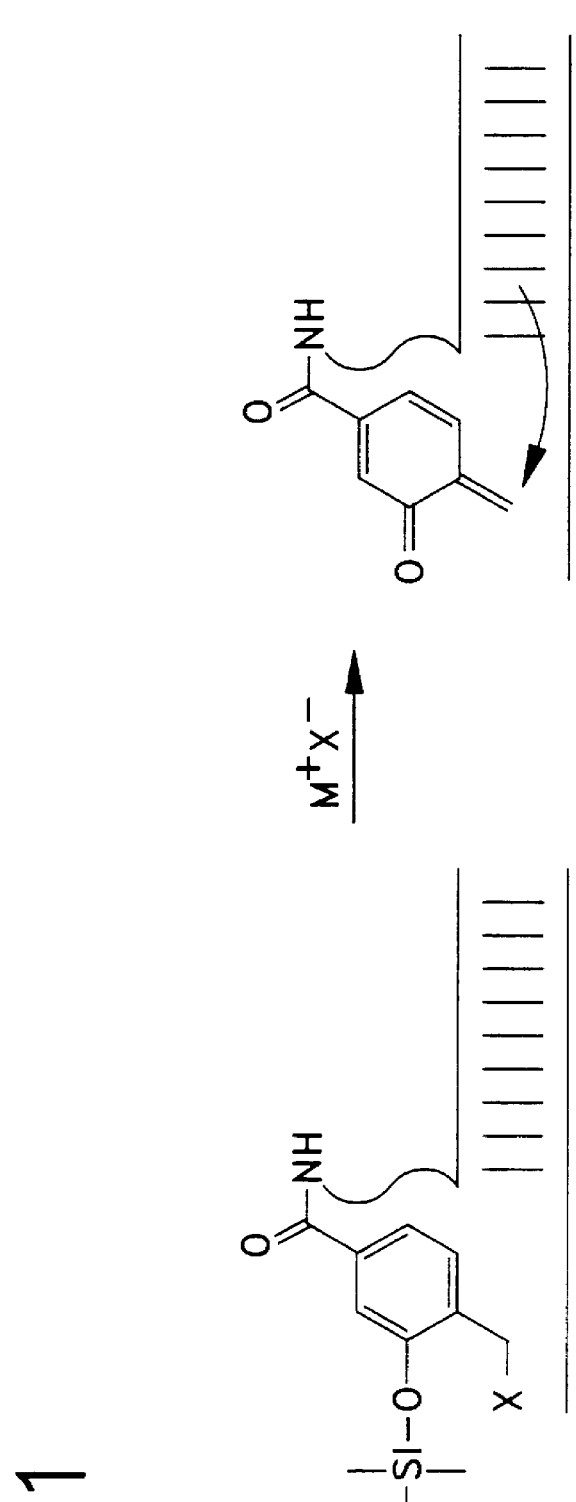
FIG. 1 illustrates ionic activation ($M^+X^-$) of a conjugated target (T) and probe (Pr) linked to a preferred silyloxy aromatic molecule to create the reactive intermediate of the present invention generated for alkylation of the target DNA.

DNA alkylation has become a mainstay of cancer chemotherapy despite the often devastating side effects of the prescribed drugs. One of the extreme examples is the nitrogen mustard mechlorethamine which must be administered by intravenous injection to prevent severe reaction with locally exposed tissue. Gilman et al., "The Pharmacological Basis of Therapeutics", 6th ed. Macmillan, New York (1980), Ch. 55. This compound is so reactive that it will decompose within minutes by reacting with cellular constituents and even water. A more controlled reaction may be achieved through the use of compounds requiring cellular activation as a prerequisite to DNA alkylation. In this manner, the undesirable side reactions of an active agent may be minimized prior to its entry into a cell. For example, cyclophosphamide must be oxidatively metabolized before DNA modification may occur and consequently, this drug exhibits a much lower acute toxicity. Similarly, mitomycin requires a reductive conversion before it can derivatize and cross-link nucleic acids.

The consummate alkylating agent for chemotherapy has yet to be developed. All currently prescribed alkylating agents suffer in part from unavoidable side reactions with non-target components of a cell or organism. Despite the use of various strategies to minimize the deleterious effects of these agents, none has overcome the necessity of generating a reactive species at some distance from the intended site of modification. Even the most selective drugs that require metabolic activation cannot overcome problems associated with the necessary diffusion of a highly reactive species to a cell nucleus and finally to its chromosomes. During this time, all nucleophilic components, not just DNA, are subject to modification. A superior compound would instead have the ability to diffuse to DNA in a latent form and become reactive only when bound within the structure of DNA. We have developed silyloxy aromatic derivatives as latent alkylating agents for in vitro DNA probe technologies. Removal of the silyl group and unmasking of the reactive agent was predicted and confirmed to proceed with addition of fluoride ion. However, the local environment established by duplex DNA also promotes the spontaneous solvolysis and elimination of the silyl group in the absence of fluoride. This exceptional result is only detected in the presence of duplex DNA. Single strands do not have the capacity to activate the silyl derivative. Therefore, the latent appendage is transformed into a powerful alkylating agent solely by its association with duplex DNA.

The invention further contemplates the use of silyloxy aromatic compounds as non-specific DNA alkylating agents. If non-specific reaction is desired, as it is in most types of chemotherapeutics, then a probe that localizes the silyloxy aromatic compound next to DNA, with limited or no regard for any specific DNA sequence, is sufficient. Two non-limiting examples of such probes include distamycin, a compound that binds relatively non-specifically to the minor groove of duplex DNA, and acridine, an intercalator that inserts non-specifically into the double helical structure of duplex DNA.

Alternatively, the linker-probe moiety could be dispensed with entirely, in situations where non-specific reaction is desired, if the silyloxy compound itself has appreciable affinity for duplex DNA. Such silyloxy compounds would include, for example, fused and planar ring systems of 3 or more rings, such as anthracenes and phenanthrenes.

Upon analysis of the chemical basis of salt-induced DNA alkylation, other related silyloxy aromatic compounds in accordance with the present invention have been identified. These compounds are "latent" alkylating agents, i.e., they are essentially unreactive except when activated with salts and in the presence of duplex DNA.

At least two independent mechanisms of activation of these compounds have been observed. A fluoride-dependent mechanism occurs in the manner described elsewhere herein. This is a very efficient and apparently universally applicable method for promoting DNA alkylation. Data indicate that this mechanism induces alkylation by model silyloxy aromatic reagents, by silyloxy aromatic-linker-probe complexes, and by the complexes hybridized to target DNA.

An alternative mechanism involves the mediation of alkylation by the ionic strength of the environment. Ionic strength alone, in the absence of fluoride, can induce alkylation of duplex DNA. However, this mechanism is also less efficient than the fluoride-dependent mechanism, requiring more time to produce an equivalent degree of alkylation. The ionic strength-dependent mechanism also lacks the capacity to activate a silyloxy aromatic model compound in the absence of fluoride or duplex DNA. The ionic strength-dependent model also fails to alkylate single-stranded DNA in the absence of fluoride, while the fluoride-dependent mechanism alkylates single and double stranded DNA with substantially equal efficiency.

The ionic strength-dependent mechanism is independent of the nature of the salt (with the exception of fluoride). For example $LiClO_4$, a chaotropic agent, has been found to be as effective in inducing alkylation of duplex DNA as NaCl, despite the contrasting natures of the salts. NaCl is normally associated with increased hydrophobic interactions while $LiClO_4$ is normally associated with decreased hydrophobic interactions. Therefore, general ionic strength, not hydrophobic effect, appears to be critical to the ionic strength-dependent mechanism of DNA alkylation by the silyloxy aromatic compounds of the present invention.

In accordance with a preferred embodiment of the present invention, an aromatic derivative is conjugated to a probe which has potential for selective alkylation of target biological molecules. It is believed that the conjugated aromatic derivatives will not react indiscriminately with biological materials other than the target molecules.

The preferred silyloxy aromatic compound of the invention comprises a substituted aromatic ring system, to which have been attached a silyloxy moiety ($-OSiR_6R_7R_8$) and at least one substituted methyl group ($-CR_9R_{10}X$) in conjugation with the silyloxy moiety through the ring system, i.e., at any carbon in the ring system that participates in resonance with the oxygen of the silyloxy moiety. In the preferred embodiment $R_6$, $R_7$ and $R_8$, are alkyl or aromatic groups, most preferably $R_6$, $R_7$ are methyl groups while $R_8$ is a t-butyl moiety. $R_9$ and $R_{10}$ are H or an alkyl or aromatic group. If more than one $-CR_9R_{10}X$ group occupies a position on the ring system in conjugation with the silyloxy moiety, then the $-CR_9R_{10}X$ moieties need not be identical, with $R_9$, $R_{10}$ and X being selected independently of the $R_9$, $R_{10}$ and X of other $-CR_9R_{10}X$ moieties.

The silyloxy aromatic derivatives of the present invention contain at least one substituted aromatic center, such as a substituted benzene ring. If more than one aromatic ring is included, the rings are preferably fused, such as naphthalenes, anthracenes, and phenanthrenes. One or more rings may optionally be heterocyclic, containing a ring member other than carbon, such as oxygen or nitrogen, while preserving the aromatic character of the ring suitable heterocyclic aromatics systems include, for example, quinolines, azanthracenes, and azaphenanthrenes.

A novel aromatic alkylating probe composition may have the following generalized formula:

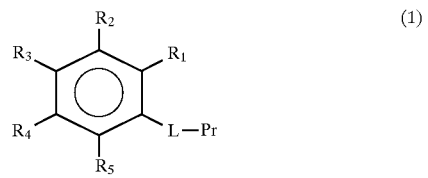

When
  $R_1=-OSiR_6R_7R_8$, then $R_2$ and/or $R_4$ can be$=CR_9R_{10}X$.
When
  $R_2=-OSiR_6R_7R_8$, then $R_1$, $R_3$ and/or $R_5$ can be$=-CR_9R_{10}X$.
When
  $R_3=-OSiR_6R_7R_8$, then $R_2$ and/or $R_4$ can be$=-CR_9R_{10}X$.
When
  $R_4=-OSiR_6R_7R_8$, then by symmetry $R_4$ is equivalent to $R_2$ as described above.
When
  $R_5=-OSiR_6R_7R_8$, then by symmetry $R_5$ is equivalent to $R_1$ as described above.
  $R_6$, $R_7$, $R_8$=various alkyl or aromatic groups;
    X=leaving group, and
Wherein $R_9$ and $R_{10}$ can be H, or an organic derivative, such as an aliphatic group or an alkyl group.

In which $CR_9R_{10}X$ is positioned on any of the carbon atoms of the ring structure; L is a linking group for attachment to a probe which may be positioned at any carbon atom of the ring, and Pr is a probe for binding to a target molecule. Preferably, the targeted alkylating agent of the present invention has the general formula:

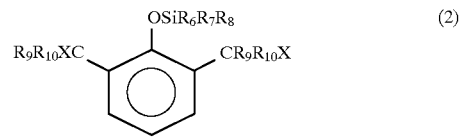

The alkylating agent need not be restricted to a single aromatic ring. For example, the agent may have a fused multi-ring structure, such as a substituted naphthalene:

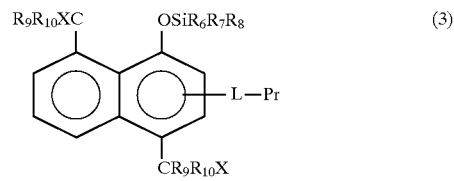

or, a substituted anthracene:

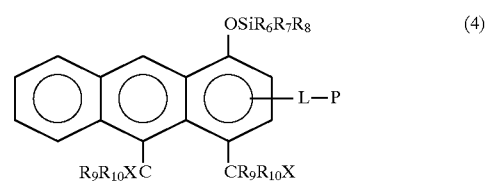

Alternatively, the alkylating agent may have a ring structure comprising more than one aromatic ring, including one or more heterocyclic aromatic rings, such as acridine, a well known intercalator:

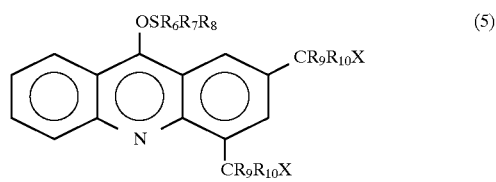

The targeted alkylating agent, optionally linked to a localizing probe, is then introduced into a system containing the target molecule to allow the alkylating agent and/or the probe to associate, i.e. hybridize, with the target molecule and to thereby localize the silyloxy aromatic derivative near the target molecule. The targeted alkylating agent is activated by ionic strength, which causes covalent bonding between the silyloxy aromatic derivative and the target molecule. If a probe is used, the covalent bonding occurs at a site proximal to the association site of the probe.

In these embodiments, the silyloxy aromatic probe alkylates a target molecule after activation by an ionic signal. In these embodiments, X is a leaving group connected to an alkyl chain positioned on an aromatic ring structure. The alkyl chain is connected at one end to the aromatic ring and includes $R_9$, an organic derivative.

Thus X may include a leaving group, such as Cl, Br, F, I, —OCOR, —OH, —OSO$_2$CH$_3$, —OSO$_2$C$_6$H$_4$CH$_3$—p, —OR, —OCONHR, —OCONHCH$_2$CH$_2$R, —OC$_6$H$_4$NO$_2$ (nitrophenol), —OC$_6$H$_5$ (phenol), and —SC$_6$H$_5$ (thiophenol).

In all of these compositions, the linking group L is made up of a chain —$R_{10}$—$R_{11}$—$R_{12}$—. Generally, the $R_{10}$ group may include a group for linking to the silyloxy aromatic derivative including NH, S, O or CH$_2$. The $R_{11}$ group can include any spacer group which can link $R_{10}$ and $R_{12}$, such as an alkyl chain. The $R_{12}$ group is any group which can link to a modified oligonucleotide or other probe Pr, examples of these are —NH$_2$, —SH, —OH and —COOH. The probe Pr includes any localizing moiety, such as an oligonucleotide, protein, intercalator, or other molecule that preferentially localizes to an organic molecule, including DNA, RNA, or protein. The oligonucleotide, whether DNA or RNA may be linked to $R_{12}$ at either its 5' or 3' terminus.

Alternatively, the oligonucleotide may be linked to $R_{12}$ at any oligonucleotide base, or phosphoribose backbone suitably modified in accordance with methods well known to those persons skilled in the art. Examples include methods described by the following publications:

1. Brakel, Ed., "Discoveries in Antisense Nucleic Acids", *Gulf Publishing Company*, Houston (1989).
2. Englisch et al., "Chemically Modified Oligonucleotides as Probes and Inhibitors", *Angewandte Chemie Int. Ed.*, 30, 613–722 (1991).
3. Nielsen, "Sequence-Selective DNA Recognition by Synthetic Ligands", *Bioconjugate Chemistry*. 2, 1–12 (1991).
4. Uhlmann et al., "Antisense Oligonucleotides: A New Therapeutic Principle", *Chemical Reviews*, 90, 543–584 (1990).
5. Goodchild, "Conjugates of oligonucleotides and Modified Oligonucleotides: A Review of Their Synthesis and Properties", *Bioconjugate Chemistry*, 1, 165–187 (1990).
6. Gebeyehu et al., "Novel Biotinylated Nucleotide-Analogs for Labelling and Colorimetric Detection of DNA", *Nucl. Acids Res.*, 15, 4513–4534 (1987).
7. Jager et al., "Oligonucleotide N-Alkyl-phosphotamides: Synthesis and Binding to Polynucleotides", *Biochemistry*, 27, 7237–7246 (1988).
8. Cocuzza, "Total Synthesis of 7-Iodo-2', 3'-Dideoxy-7-Deazapurine Nucleosides, Key intermediates in the Preparation of Reagents for the Automated Sequencing of DNA", *Tet. Lett.*, 29, 4061–4064 (1988).
9. Hanna et al., "Synthesis and Characterization of 5-[(4-Azidophenacyl)thio]uridine 5'-Triphosphate, a Cleavable Photo-Cross-Linking Nucleotide Analogue", *Biochemistry*, 28, 5814–5820 (1989).
10. Gibson et al., "Synthesis and Application of Derivatizable Oligonucleotides", *Nucl. Acids Res.*, 15, 6455–6467 (1987).
11. Nelson et al., "A New and Versatile Reagent for Incorporating Multiple Primary Aliphatic Amines Into Synthetic Oligonucleotides", *Nucl. Acid Res*, 17, 7179–7186, (1989).

In a preferred embodiment of the invention, described in Examples 1 and 2, the silyloxy aromatic alkylating probe is activated by an ionic signal. For in vitro use the preferred ionic signals are KF, NaF, CsF and other salts (MX), defined as salts of a metal (M) and an anion (X). These, however, are not the only possible ionic triggering agents. Rather, the triggering signal is dependent on a general increase in ionic strength. Accordingly, silyl-containing reactive centers, such as Si:$R_6R_7R_8$, as defined above, can be used for both in vitro and in vivo uses.

A preferred embodiment of the present invention has the following structure:

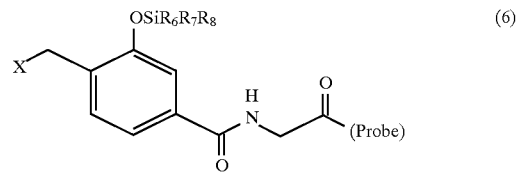

(6)

Another embodiment (7) which was attempted includes:

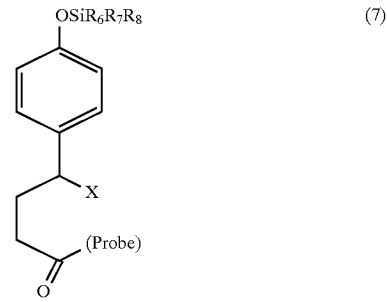

(7)

This embodiment, however, proved too reactive.

Another embodiment (8) was attempted, but it did not couple well to the probe:

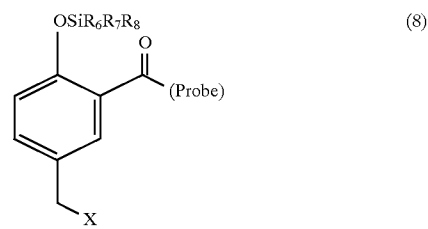

(8)

Another embodiment (9) was too unreactive, as it would only work in non-aqueous systems:

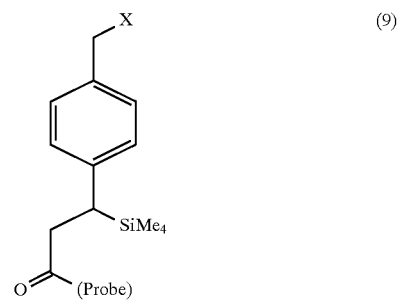

(9)

The present invention also describes a process for selectively alkylating a target molecule. A great number of useful clinical and laboratory applications for which this process may be applied are described for somewhat related processes in PCT published Application No. WO 85/02628 to Yabusaki et al., the disclosure of which is incorporated by reference herein. Also the process of Reverse Southern Blotting is described generally in the Background of the Related Art, supra.

Generally, the process of this invention may be carried out by first providing a probe for recognizing a predetermined binding site on a target molecule. The probe may include a strand of DNA, RNA, or a protein. See, for example, Praseuth et al., "Sequence-Specific Binding and Photo-crosslinking of α and β oligodeoxy-nucleotides to the Major Groove of DNA via Triple-Helix Formation", *Proc. Natl. Acad. Sci. USA*, 85, 1349–1353 (1988). Alternatively it may include any other molecule which can localize the probe to a target molecule. For example, Dervan, "Design of Sequence-Specific DNA-Binding Molecules", *Science*, 232, 464–471 (1986), describes a variety of natural and synthetic compounds that bind DNA in a sequence-specific manner and which comprise a series of subunits linked by peptide bonds. Among these compounds potentially useful as probes in accordance with the invention is actinomycin, which acts as an intercalator by means of a phenoxazone moiety, and binds 4 base pairs above and below the intercalation site by means of identical cyclic pentapeptide lactones. Actinomycin exhibits a preference for 5'-NGCN-3' sequences. The Dervan article also describes an alternative mode of peptide binding to double-helical DNA, such as the minor groove sequence specific binding exhibited by distamycin, a crescent-shaped tripeptide containing three N-methylpyrrole carboxamides linked by peptide bonds. In addition, Dervan describes comparable sequence-selective binding of oligopeptides having up to 7 amide groups. Dervan also describes synthetic sequence specific probes utilizing a combination of intercalation and minor groove binding as the means for identifying double-helical DNA sequences up to 10 base pairs in length. The Dervan article illustrates that it is well known in the art that a probe useful for the invention may optionally be an intercalating moiety, a peptide of variable length and structure or even a combination of the two sorts of localizing molecule.

The Dervan publication also mentions the binding of organometal complexes to DNA. This type of localizing molecule is further described in a review by Barton entitled "Metals and DNA: Molecular Left-Handed Complements", *Science*, 233, 727–734 (1986). The Barton publication describes chiral metal complexes capable of various structural interactions with DNA including stereoselective intercalation, groove binding, and direct coordination. Such metal complexes may be useful as probes in accordance with the present invention.

The process carried out by providing a silyloxy aromatic derivative, which may be modified for linking to the probe molecule if desired. The probe is then linked to the silyloxy aromatic derivative to create a targeted alkylating agent. The target alkylating agent is introduced into a system containing a target molecule, and the probe associates with the target molecule localizing the linked silyloxy aromatic derivative near the target molecule. As illustrated in FIG. 1, crosslinking or covalent bonding is then initiated by activating the targeted alkylating agent by an ionic signal, such as KF, other salts MX, or the ionic signal can be the naturally occurring high ionic strength region localized around polyanionic nucleic acids. A covalent bond is then formed between the aromatic derivative and the target, proximal to the association site of the probe with the target molecule.

In one preferred embodiment, the linking step includes a step of adapting the silyloxy aromatic derivative by the addition of an acidic linking group which is capable of being modified for linking to the probe molecule. Preferably, the silyloxy aromatic derivative includes at least one arm, —CR$_9$R$_{10}$X, attached to the aromatic ring, and in conjugation through the ring with the silyoxy moiety.

Ideally, drugs targeted at nucleic acid should be able to modify DNA or RNA sequences specifically and efficiently. Specific modification of target sequences can be achieved by using "antisense" or "triplex forming" techniques in which oligonucleotides are used to interfere with DNA or RNA functions. Alternatively, probes may be used which target nucleic acids but which are not directed to specific sequences.

However, a number of factors are known to impede such techniques. Among these factors is that the exogenous oligonucleotide must travel to the target cell, must traverse the cell membrane, must find its target RNA or DNA in the cytoplasm or nucleus, must bind with high affinity and specificity, and must exert the desired biological effect for the desired period of time. To improve cellular uptake, stability, and affinity, an agent can be formed by conjugating a functional group with an oligonucleotide. Optimally, the functional group would have activity which is induced solely by the target, i.e., only the target DNA or RNA will trigger the reaction between the agent and the target itself.

Accordingly, in another embodiment of the invention, an oligonucleotide conjugate of a silyl phenol ether which is a latent o-quinone methide precursor has been developed apparently possessing this targeted inducible activity.

This conjugate has the following structure:

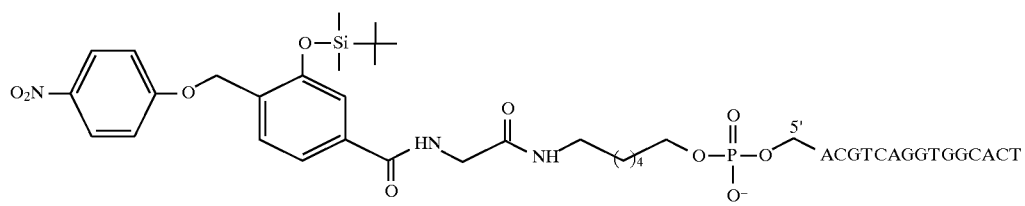

(10)

This conjugate was developed as a latent alkylating agent for use as an in vitro DNA probe. The DNA target modification was induced by fluoride ion, which was believed to promote the o-quinone methide intermediate formation. The desilylation apparently proceeds as follows:

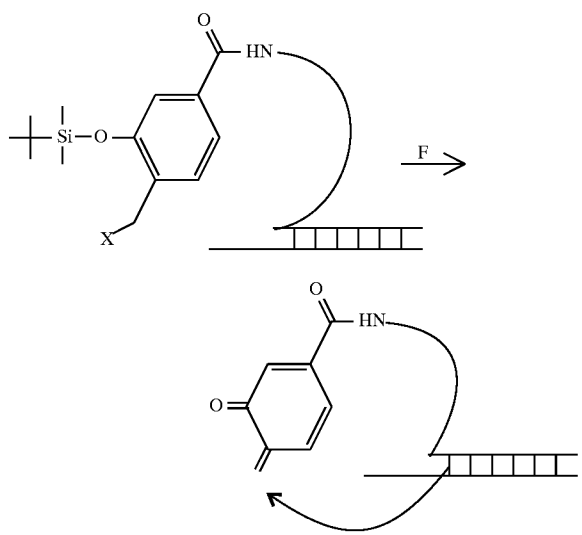

DNA alkylation was also observed to take place in the presence of non-fluoride salts such as KCl, KBr, KClO$_4$, NaCl, NaBr, NaClO$_4$, LiClO$_4$, MgCl$_2$, and potassium phosphate. This list of salts is illustrative but not exhaustive of the salts which are useful for the invention. In this situation the alkylation and cross-linking of the target strand of DNA with the conjugate may have a different mechanism from that reaction induced by the fluoride salt.

A model compound, the synthesis of which is described in Example 7, was designed to study the mechanism of fluoride induced DNA alkylation. In particular, the reactivity of the functional group moiety to nucleophiles such as DNA bases or the solvent are capable of being studied using this model compound. The model compound was synthesized and its solvolysis in the presence of fluoride salts, non-fluoride salts, and nucleoside was studied kinetically by $^1$H NMR (Example 8) and UV-VIS spectroscopy (Example 9).

Results of these analyses showed that only fluoride ion is capable of deprotecting the phenol hydroxy group and further promoting solvolysis of the model compound. It was also observed that non-fluoride salts and a nucleoside had no effect on solvolysis of the model compound.

These results were consistent with in vitro experimental results which showed that alkylation and cross-linking of target DNA with conjugate occurs in the presence of non-fluoride salts only when the silyloxy aromatic compound associates with duplex DNA or when the target has been previously hybridized with the conjugate. See Examples 1–5. It is possible that a unique conformational microenvironment is formed which requires the hybridization of the target DNA with the conjugate with the aid of salts. It is believed that this microenvironment facilitates the generation of the quinone methide for the nucleophilic reaction between the DNA bases and the functional group of the conjugate to produce the cross-linked product.

If in vivo use is desired, then suitably modified probes capable of traversing cell membranes may be prepared, as well known to those skilled in the art, for example, as described by Blake et al., "Hybridization Arrest of Globin Synthesis in Rabbit Reticulocyte Lysates and Cells by Oligodeoxyribonucleoside Methylphosphonates", *Biochemistry*, 24, 6139–6145 (1985); and by Agrawal et al., "Oligodeoxynucleoside Phosphoramidates and Phosphorothioates as Inhibitors of Human Immunodeficiency Virus", *Proc. Nat'l. Acad. Sci. U.S.A.*, 85, 7079–7083 (1988). These probes are then attached to the activated esters.

The following Examples further illustrate the various features of the invention, and are not intended in any way to limit the scope of the invention, which is defined in the appended claims.

In these Examples, we have shown that a preferred probe, as described above, causes selective alkylation of a DNA target, which has been ionically activated after the probe has hybridized with the target DNA sequence.

EXAMPLE 1

Preparation of Silyloxy Aromatic Ionically Inducible Alkylating Linked Probe

An ionic induced silyloxy aromatic alkylating linked probe was prepared in accordance with the invention. The probe was tested in vitro using a synthetic DNA target strand. The steps followed in the synthesis of a representative silyloxy aromatic ion-induced alkylating probe for coupling to the 5' terminus of an oligonucleotide are generally shown in Scheme A.

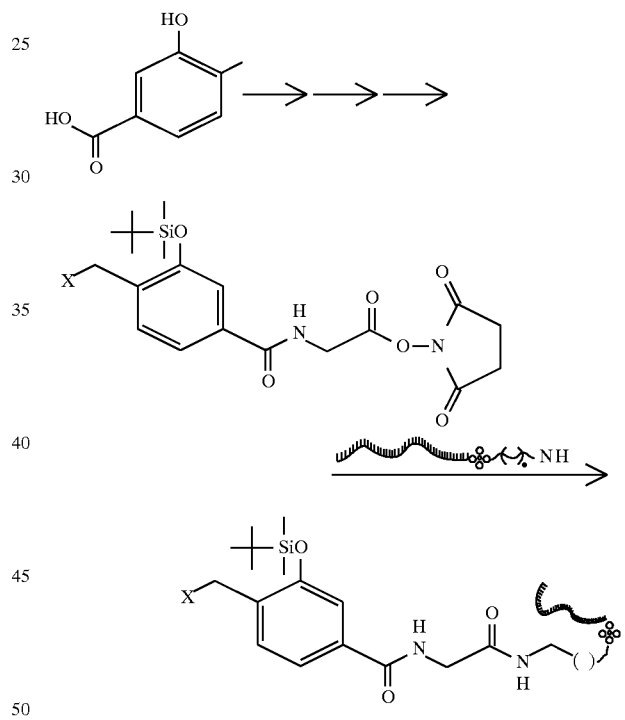

A parallel series of steps followed in the synthesis of a representative silyloxy aromatic ion induced alkylating probe for coupling to the 3' terminus of an oligonucleotide are shown in Scheme B.

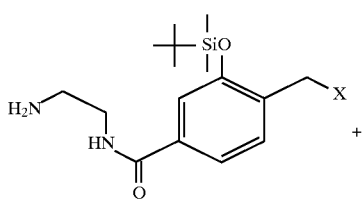

-continued
Scheme B

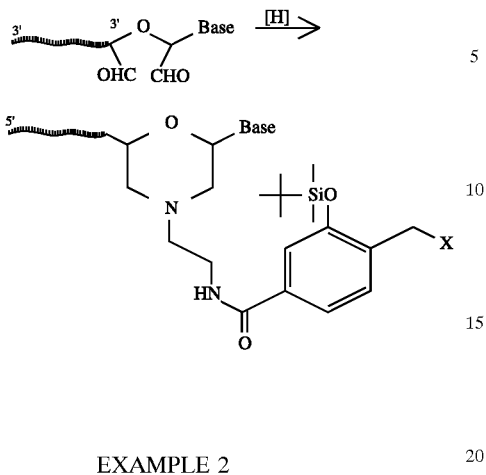

EXAMPLE 2

Preparation of the preferred silyloxy aromatic system suitable for coupling to a probe-linker species (L-Pr)

The following general Scheme (Scheme 1) illustrates the steps taken in the synthesis of preferred silyloxy aromatic molecules which are suitable for coupling to probe (Pr) - linker (L) species, and directing the ionically inducible covalent crosslinking system to a desired target (T). The method described in Scheme 1 is general enough for the preparation of a number of useful derivatives of Compound 1.7.

SCHEME 1

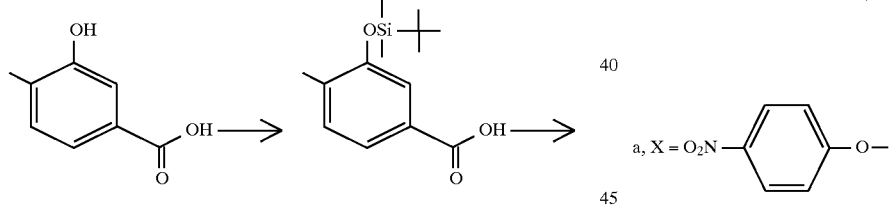

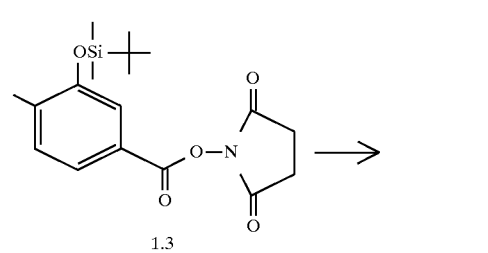

-continued
SCHEME 1

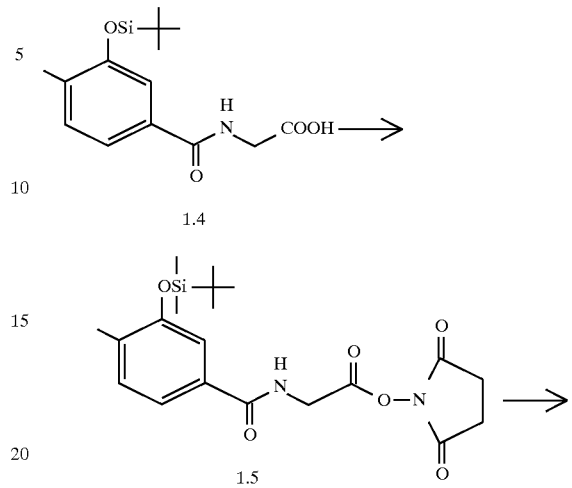

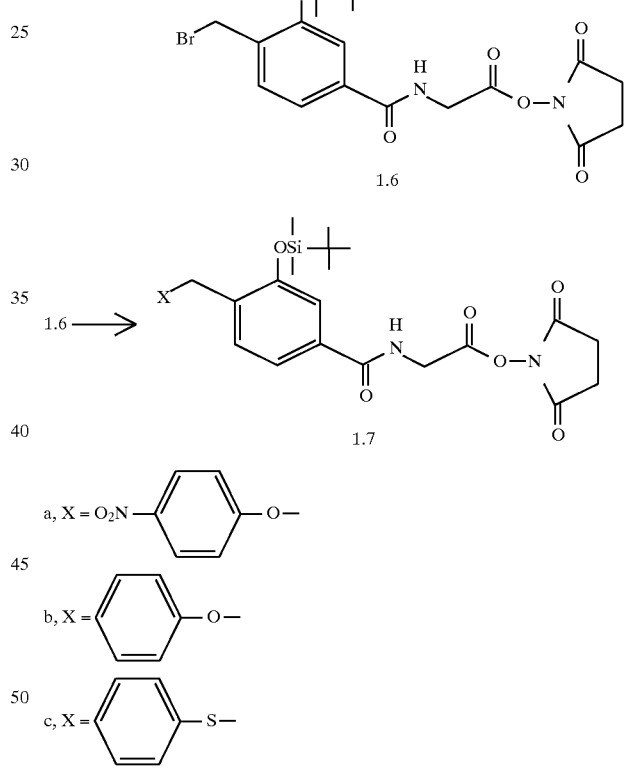

Protocol 1.1: Synthesis of the Silyl Protected 1,2,5-Trisubstituted Phenol

Materials and Methods for the Synthetic Procedures

Proton magnetic resonance ($^1$H NMR) spectra were recorded on a QE-300 spectrometer. Chloroform-d was used as a solvent and TMS as reference. UV/VIS spectra were measured with a Perkin-Elmer Lambda 5 spectrophotometer, and mass spectra were obtained with a HP 598A mass spectrometer. Flash chromatography is a commonly used purification technique described by Still et al., *J. Org. Chem.*, 43, 2923–2925 (1978), and 230–400 mesh silica gel was used. Thin-layer chromatography (TLC)

analysis utilized Machery-Nagel polygram Sil G/UV silica gel plates. Tetrahydrofuran (THF) was distilled from sodium, and acetonitrile was distilled from $CaH_2$ immediately prior to use. Dimethyl formamide (DMF), $CCl_4$ and triethylamine were stored over Linde 4-A molecular sieves at least two days prior to use. Other materials identified in these Examples were obtained from commercial suppliers and used without further purification.

3-t-Butyldimethylsiloxyl-4-methylbenzoic acid (Compound 1.2)

t-Butyldimethylsilyl chloride (3.32 g, 22.1 mmol) was added to a solution of Compound 1.1 (1.12 g, 7.4 nmol) and triethylamine (1.79 g, 16.2 mmol) in 30 mL THF. The mixture was heated at 40° C. overnight. After the reaction mixture was allowed to cool to room temperature, the triethylammonium chloride was filtered out. The filtrate was then diluted with ether (50 mL) and a few drops of distilled water was added and stirred at room temperature for five hours. After evaporation of the solvent, the product was purified by flash silica chromatography (ethyl acetate:hexanes=1:3) to yield 1.60 g (81.5%) of a white solid: $^1$H NMR $\delta$7.49 (s, 1H), 7.39 (s, 1H), 7.11 (d, 1H), 2,20 (s, 3H), 0.96 (s, 9H), 0.31 (s, 6H).

3-t-Butyldimethylsiloxyl-4-methylbenzoic acid N-hydroxysuccinimide ester (Compound 1.3)

Dicyclohexylcarbodiimide (DCC, 1.17 g, 5.7 mmol) was added to a solution of N-hydroxysuccinimide (0.28 g, 7.1 mmol) and Compound 1.2 (1.27 g, 4.8 mmol) in DMF (50 mL) and stirred overnight at 4° C. This mixture was then diluted with ether (50 mL) and water (50 mL), filtered and concentrated. The remaining residue was purified by flash silica chromatography (ethyl acetate:hexanes=1:3) to yield 1.13 g (65.3%) of a white solid: $^1$H NMR $\delta$7.60 (d, 1H), 7.41 (s, 1H), 7.18 (d, 1H), 2.83 (s, 4H), 2.23 (s, 3H), 0.96 (s, 9H), 0.18 (s, 6H). LRMS m/z 363 (M$^+$), 217, 189, 85.

N-(3-t-Butyldimethylsiloxyl-4-methylbenzoyl) glycine (Compound 1.4)

An aqueous solution (50 mL) of glycine (0.11 g, 1.5 mmol) was combined at room temperature with a solution of Compound 1.3 (0.44 g, 1.2 mmol) in acetonitrile (50 mL) and triethylamine (0.14 g, 1.2 mmol). This mixture was manually shaken for two minutes and then washed with ether (50 mL). The aqueous phase was acidified to pH 2 with 6 N HCl and extracted with ether (3×50 mL). The combined organic phases were evaporated and the product was purified by flash silica chromatography (ethyl acetate:hexanes=1:1) to yield 0.31 g (74.6%) of a white solid: $^1$H NMR $\delta$7.26 (m, 3H), 6.64 (m, 1H), 4.02 (d, 2H), 2.20 (s, 3H), 0.98 (s, 9H), 0.22 (s,6H). LRMS m/z 323 (M$^+$), 221, 149, 99.

N'-(3-t-Butyldimethylsiloxyl-4-methyl-benzoyl) glycine-N-hydroxysuccinimide ester (Compound 1.5)

The method described for the synthesis of Compound 1.3 was also used to produce Compound 1.5 (62.2% yield). $^1$H NMR $\delta$7.24 (m, 3H), 6.50 (m, 1H), 4.59 (d, 2H), 2.86 (S, 4H), 2.24 (s, 3H), 1.01 (s, 9H), 0.24 (s,6H). LRMS m/z 420 (M$^+$), 348, 190.

N'-(3-t-Butyldimethylsiloxyl-4-(bromomethyl) benzoyl) glycine N-hydroxysuccinimide ester (Compound 1.6)

N-bromosuccinimide (NBS) (0.07 g, 0.4 mmol) was added to a solution of Compound 1.5 (0.12 g, 0.29 mmol) in $CCl_4$ (10 mL). The mixture was then maintained at 20° C. and irradiated with a 275 W sunlamp (Sears, #34-7105) for fifteen minutes. After the solid succinimide was filtered away, the filtrate was evaporated. The remaining residue was purified by flash silica chromatography (ethyl acetate:hexanes=1:3) to yield 0.08 g (58.9%) of a white solid. $^1$H NMR $\delta$7.26 (m, 3H), 6.76 (m, 1H), 4.60 (d, 2H), 4.50 (s, 2H), 2.86 (s, 4H), 1.01 (s, 9H), 0.31 (s, 6H). LRMS m/z 344, 342, 263, 245.

N'-[3-t-Butyldimethylsiloxyl-4-(p-nitrophenoxy) benzoyl]glycine N-hydroxysuccinimide ester (Compound 1.7a)

Potassium p-nitrophenolate (0.02 g, 0.2 mmol) was added to a solution of Compound 1.4 (0.08 g, 0.2 mmol) in freshly distilled acetonitrile (2 mL). The mixture was stirred at room temperature for one hour and then water and ether (10 mL of each) were added. The aqueous phase was washed with 3×10 mL of ether. The combined ether fractions were dried and the remaining residue was purified by flash silica chromatography to yield a yellowish solid (0.05 g, 59.4%). $^1$H NMR $\delta$8.32 (d, 2H), 7.60 (d, 2H), 7.37 (m, 3H), 6.52 (m, 1H), 5.53 (d, 2H), 5.18 (s, 2H), 2.67 (s, 2H), 1.02 (s, 9H), 0.30 (s, 6H). LRMS m/z 419, 349, 275, 189.

N'-[3-t-Butyldimethylsiloxyl-4-(phenoxymethyl) benzoyl]glycine N-hydroxysuccinimide ester (Compound 1.7b)

Potassium phenolate (0.01 g, 0.1 mmol) was added to a solution of Compound 1.6 (0.02 g, 0.1 mmol) in freshly distilled acetonitrile (2 mL). The mixture was stirred at room temperature for one hour and water and ether (10 mL of each) were added. The aqueous phase was washed 3×10 mL of ether. The combined ether fractions were dried and the remaining residue was purified by flash silica chromatography to yield a white solid (0.01 g, 49%). $^1$H NMR $\delta$7.56 (d, 2H), 7.32 (m, 6H), 6.72 (m, 1H), 5.17 (s, 2H), 4.60 (d, 2H), 2.66 (s, 4H), 1.01 (s, 9H), 0.29 (s, 6H).

N'-[3-t-Butyldimethylsiloxyl-4-(thiophenoxymethyl) benzoyl]glycine N-hydroxysuccinimide ester (Compound 1.7c)

This was synthesized under equivalent procedure as described for Compound 1.7a and Compound 1.7b, above, the adaptation of which is well within the knowledge of those skilled in the art. $^1$H NMR $\delta$7.37 (m, 8H), 6.60 (m, 1H), 4.52 (d, 2H), 4.04 (s, 2H), 2.82 (s, 4H), 0.95 (s, 9H), 0.23 (s, 6H).

Protocol 1.2: Coupling the reactive centers (Compound 1.7) to a sequence directing oligonucleotide-linker (L-Pr)

Materials and methods for coupling Procedures

Oligonucleotides were synthesized by standard solid phase phosphoramidite methods on a Dupont Coder 300 (Department of Pharmacology, SUNY at Stony Brook) and on a Biosearch instrument by Clontech Laboratories, Inc. (Palo Alto, Calif.). When necessary, the oligonucleotides were also purified and deprotected by standard procedures. Reverse phase (C-18) separation and analysis utilized a Varian 5000 HPLC controller, Varian 2050 variable wavelength detector, Hewlett Packard 3390A recording integrator and Spherex 5 $\mu$M C-18 column (Phenomenex). UV/VIS spectra were recorded on a Perkin Elmer Lambda-5 spectrophotometer.

Preparation of the oligonucleotide (Pr) derivatized at the 5' end with a hexamethylamino group (L-Pr)

The hexamethylamino linker was attached to the 5' end of the nascent oligonucleotide (Pr, ACGTCAGGTGGCACT)

during the last step of the solid phase synthesis by using a monomethyoxytrityl protected hexamethylamino precursor (N-MMT-CG-AminoModifier supplied by Clontech Laboratories, Inc.). The protecting group was released after the complete synthesis by treating the crude material with 80% acetic acid for 30 minutes. The free trityl derivative was removed by ether extraction and the oligonucleotide aminolinker derivative was stored as an aqueous solution (−20° C.) before coupling to the reactive centers.

Coupling the activated ester (Compound 1.7a) to the aminolinker oligonucleotide probe (L-Pr)

A solution of 2 mg 1.7a in DMF (200 μL) was combined with a solution of L-Pr ($A_{260}$=3.0 absorbance units [AU]) in 0.25M 3-(N-morpholino)-propanesulfonic acid at pH 7.5) (200 μL). This mixture was left undisturbed at 4° C. for 5 hours. The coupled product, designated Compound 1.7a-L-Pr, was purified by reverse phase (C-18) chromatography using a gradient of 10% acetonitrile in 45 mM triethylammonium acetate pH 6 to 30% acetonitrile in 30 mM triethylammonium acetate pH 6 over 30 min (1 mL/min). The desired material eluted with a retention time of 23 min and, after collection, was immediately frozen and dried under high vacuum (20% yield based on recovered $A_{260}$).

Protocol 1.3: Preparation of target (T) and Modification of T with the reagent Compound 1.7a-L-Pr The target strand (T, AGTGCCACCTGACGTCTAAG) was prepared in the same manner as the oligonucleotide Pr described in Protocol 1.2. For product detection, T was labeled with $^{32}$p (*pT) in accordance with the procedures described by Maniatis et al., in *Molecular Cloning. A Laboratory Manual*, Cold Spring Harbor Laboratory, Cold Spring Harbor, N.Y. (1982).

Probe-target crosslinking and detection

The reaction between the probe (Compound 1.7a-L-Pr) and target sequences (T) was characterized in a standard reaction mixture (10 μL) containing 1 mM potassium phosphate pH 7, 6 nM Compound 1.7a-L-Pr and 6 nM *pT (20 nCi). Samples were incubated at 4° C. for no less than 10 min and then an aqueous solution of KF was added to a final concentration of 10–250 mM. This treatment activated the system for covalent crosslinking of the hybridized strands. This process was quenched after 10 min (4° C.) by addition of excess DNA (for example, T) and placing samples on dry ice. The volume of each sample was then reduced by 50% under high vacuum and 5 μL of 80% formamide was added in preparation for electrophoretic analysis.

Figure 2:
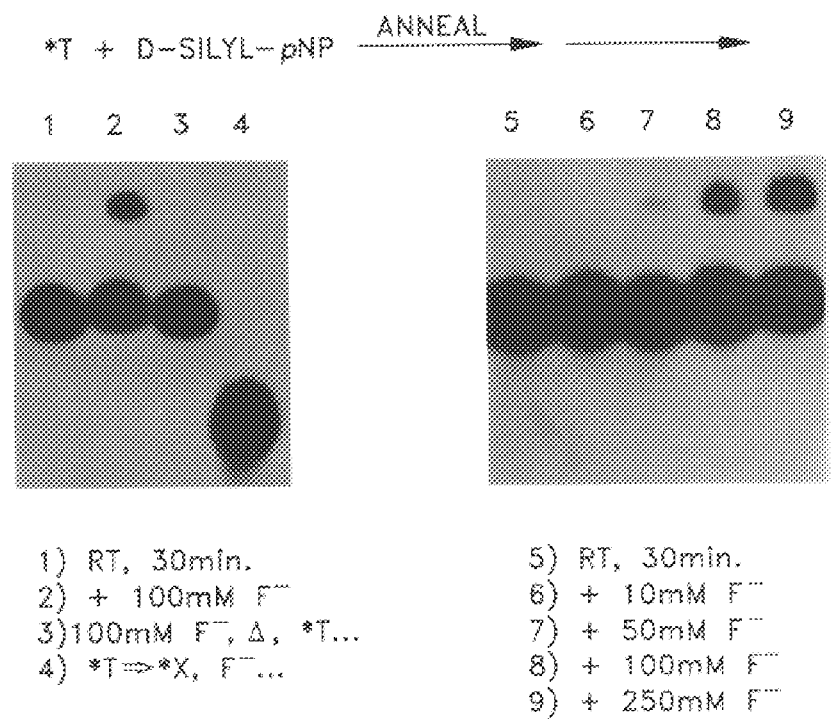
FIG. 2 is an autoradiogram of a denaturing polyacrylamide gel electrophoresis showing the ionic activated crosslinking reaction between a probe and a DNA target in accordance with the present invention, as described in Example 2, Protocol 1.3.

FIG. 2 shows an autoradiogram of a denaturing 20% polyacrylamide gel that was used to demonstrate the successful application of Compound 1.7a-L-Pr. *T is the target strand and D-silyl-pNP is Compound 1.7a-L-Pr. The concentrations, quenching and analyses are all the same as described above for FIG. 1. Reactions were carried out at room temperature for 30 minutes. Lane 1 indicates that no alkylation of the target (crosslinking) occurred in the absence of fluoride. Lane 2 is the positive control, demonstrating that the crosslinking was triggered by the presence of 100 mM fluoride. Lane 3 shows that the reagent can be neutralized by treatment with 100 mM fluoride (40° C., 30 minutes) before *T is added. Lane 4 proves that the oligonucleotide reagent is specific for complementary sequences. A non-complementary oligonucleotide (X) 14 nucleotides long ([$^{32}$P]-5'-CATGCGTTCCCGTG) did not react with Compound 1.7a-L-Pr after addition of 100 mM fluoride. For the samples in lanes 5–9, the fluoride concentration was varied from 0.0–250 mM.

Figure 3:
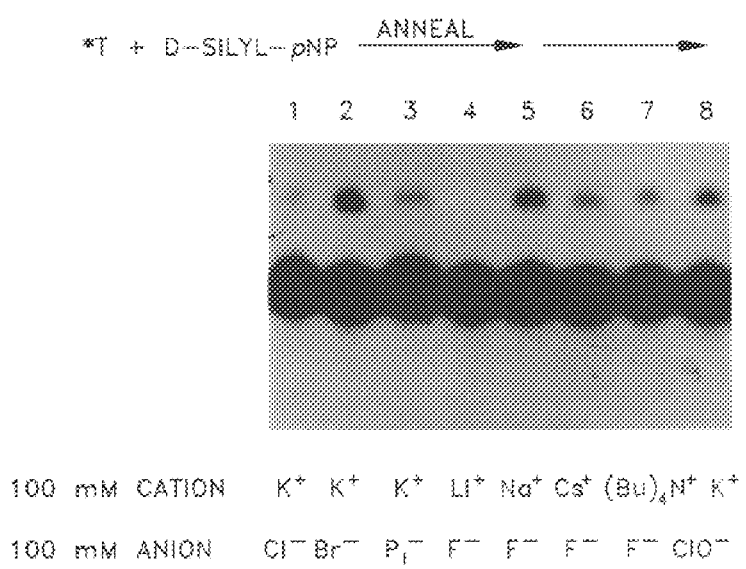
FIG. 3 is an autoradiogram showing that fluoride is not the only possible ionic triggering agent, as described in Example 2.

FIG. 3 shows that fluoride is not the only possible triggering agent. The signal for inducing reaction is not so much dependent on fluoride as it is dependent on a general increase in ionic strength. Accordingly, silyl containing reactive centers can be used for both in vivo and in vitro uses. No other ionic strength dependent covalent binding reagent has ever before been proposed or tested.

Protocol 1.4: Synthesis of reactive centers with reactivity similar to Compounds 1.7a–c By treating Compound 1.6 with various nucleophiles (X), a series of related appendages for triggered reaction were produced:

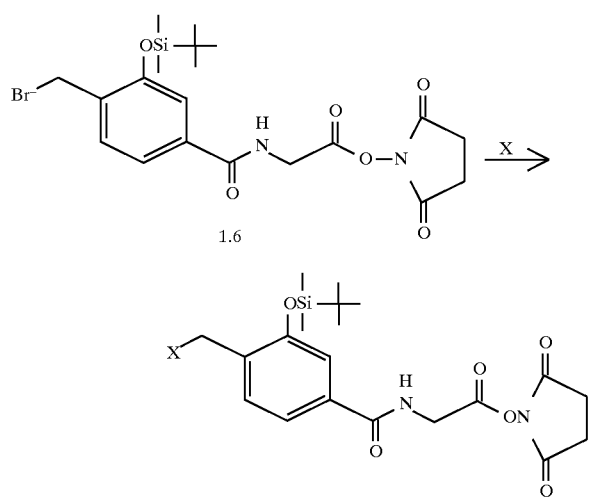

EXAMPLE 3

Reactive centers other than those represented by Compound 1.7 have been constructed for inducible and selective crosslinking of the complex formed by a probe (L-Pr) and target (T).

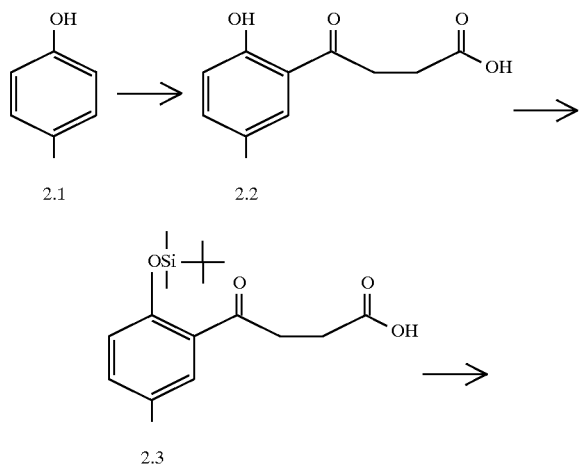

SCHEME 2

SCHEME 2 -continued

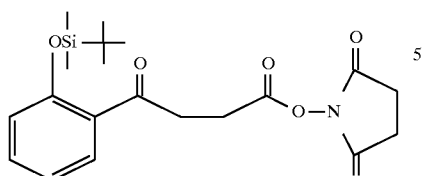

2.4

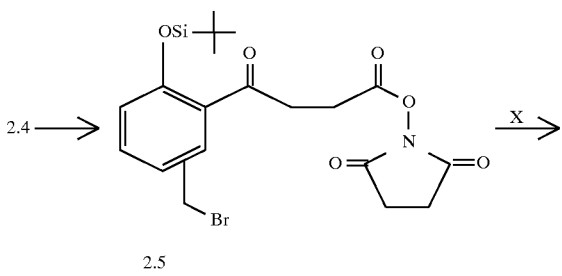

2.5

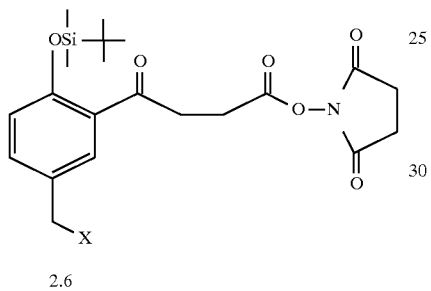

2.6

Protocol for the preparation of a reactive center designed for coupling to an aminolinker probe (L-Pr)

3-(5-methylbenzoyl)propionic acid (Compound 2.2)

This compound was prepared by the method of Raval et al., *J. Univ. Bombay*, 7Pt. 3, 184 (1983); CA 33, 3779 (1989). p-Cresol (4.0 g, 37 mmol) and succinic anhydride (3.4 g, 34 mmol) were combined in 1,1,2,2-tetrachloroethane (40 mL) and the mixture was heated to 60° C. Aluminum chloride (9.5 g, 71 mmol) was then added to the solution at a rate of 2 g/20 min. Once this was complete the reaction was heated to 135° C. for 30 min. After cooling, water and ether (30 mL of each) were added and the aqueous layer was extracted with 3×°mL of ether. The combined organic fractions were dried and the remaining residue was purified by flash silica chromatography to yield 2.2 g (28.5%). $^1$H NMR δ7.62 (s, 1H), 7.30 (d, 1H), 6.85 (d, 1H), 3.32 (t, 2H), 2.35 (t, 2H), 2.22 (s, 1H).

3-(2-t-Butyldimethysiloxy-5-methylbenzoyl) propionic acid (Compound 2.3)

t-Butyldimethylsilyl chloride (2.3 g, 18.6 mmol) was added to a solution of Compound 2.2 (1.0 g, 18.6 mmol), triethylamine (0.9 g, 8.9 mmol) and THF (15 mL) at room temperature. The reaction mixture was then stirred for three hours at 40° C. The triethylammonium chloride was precipitated and removed after addition of 10 mL ethyl acetate-:hexanes (3:1). The filtrate was separated by flash silica chromatography to yield a yellow liquid (1.45 g). This material was consistent with a disilyl derivative of Compound 2.2 and could be used directly to form the desired product. For example, an ether solution (20 mL) of this liquid (0.5 g, 1.1 mmol) was treated with two drops of water and stirred overnight at room temperature. After the solvent was removed, the product was purified on flash silica chromatography to yield a white solid (0.3 g, 81%). $^1$H NMR δ7.30 (s, 1H), 7.02 (d, 1H), 6.66 (d, 1H), 3.22 (t, 2H), 2.26 (t, 2H), 2.18 (s, 3H), 0.85 (s, 9H), 0.14 (s, 6H).

3-(2-t-Butyldimethylsiloxyl-5-methylbenzoyl) propionic acid N-hydroxysuccinimide ester (compound 2.4)

N-Hydroxysuccinimide (0.064 g, 0.31 mmol) was added to a solution of compound 2.3 (0.1 g, 0.31 mmol) in DMF (3 mL). After this mixture was cooled to 4° C., DCC (0.036 g, 0.31 mmol) was added. The reaction mixture was stirred for three hours at 4° C. and then filtered to remove the dicyclo-hexylurea. The filtrate was washed with water, dried and evaporated. The remaining residue was separated by flash silica chromatography to yield a white solid (0.096 g, 74%). $^1$H NMR δ7.14 (s, 1H), 7.11 (d, 1H), 6.73 (d, 1H), 3.37 (t, 2H), 2.93 (t, 2H), 2.77 (s, 4H), 2.22 (s, 3H), 0.92 (s, 9H), 0.21 (s, 6H).

3-(2-t-Butyldimethylsiloxyl-5-(bromomethyl) benzoyl) propionic acid N-hydroxysuccinimide ester (Compound 2.5)

NBS (0.067 g, 0.37 mmol) and Compound 2.4 (0.13 g, 0.31 mmol) were combined in $CCl_4$ (3 mL). This solution was then maintained at 20°0 C. and irradiated with a 275 W sunlamp (Sears, #34-7105) for fifteen minutes. After the solid succinimide was filtered away, the filtrate was evaporated. The residue remaining was purified by flash silica chromatography to yield a yellow solid (0.072 g, 45%). $^1$H NMR δ7.65 (s, 1H), 7.36 (d, 1H), 6.78 (d, 1H), 4.39 (s, 2H), 3.37 (t, 2H), 2.98 (t, 2H), 2.76 (s, 4H), 0.94 (s, 9H), 0.30 (s, 6H).

3-(2-t-Butyldimethylsiloxyl-5-(chloromethyl) benzoyl) propionic acid N-hydroxysuccinimide ester (Compound 2.6a)

Potassium chloride (0.68 g, 0.15 mmol) was added to a solution of Compound 2.5 (0.05 g, 0.1 mmol) in acetonitrile (5 mL). The reaction mixture was stirred for two hours at 40° C. and then washed. The organic phase was dried, evaporated and separated by flash silica chromatography to yield a white solid (0.034 g, 72%).

$^1$H NMR δ7.65 (s, 1H), 7.32 (d, 1H), 6.81 (d, 1H), 4.48 (s, 2H), 3.36 (t, 2H), 2.96 (t, 2H), 2.77 (s, 4H), 0.93 (s, 9H), 0.24 (s, 6H).

Each of these silyloxy aromatic alkylating agents can be substituted by replacing the bromo with the other X groups, such as acetate, p-nitrophenolate and the like, as described in Example 2.

EXAMPLE 4

In a generalized embodiment, the silyloxy substituent may be in direct conjugation with the —CHX— group (for example, ortho or Para when attached to a phenyl ring) and an appendage for joining the aromatic system to the linker-probe (L-Pr) may be designed in any known manner. However, not all combinations were found to be appropriate due to the intrinsic reactivity of specific arrangement of functional groups.

SCHEME 3

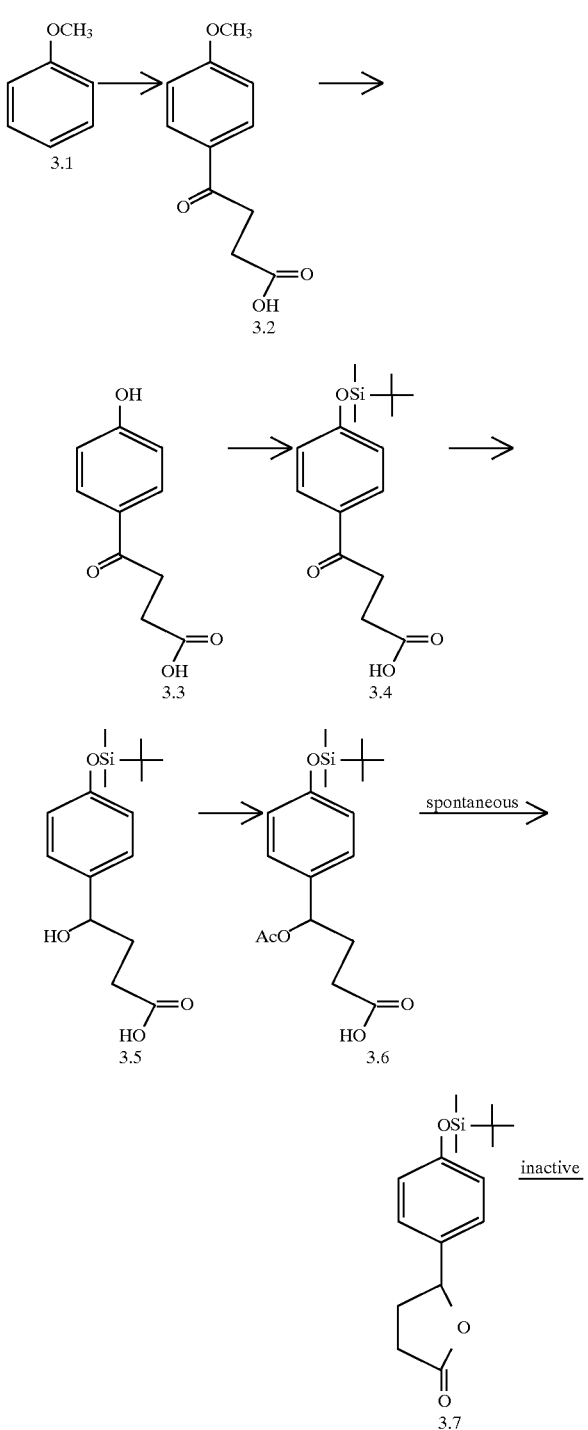

3-(4-methoxylbenzoyl)propionic acid (Compound 3.2)

A solution of p-anisole (4.32 g, 50 mmol) and succinic anhydride (4.14 g, 40 mmol) were combined in 1,1,2,2-tetrachloroethane (10 mL) and nitrobenzene (40 mL) at 4° C. Aluminum chloride (24.56 g, 180 mmol) was then added gradually. The temperature was kept at 0°–5° C. and stirred overnight. Water was added and neutralized to quench the reaction. The aqueous phase was separated and washed with ether then reacidified and washed with ether again. The ether fractions were combined, dried and evaporated. The remaining residue was purified by flash silica chromatography to yield a white solid (7.55 g, 88%). $^1$H NMR (CDCl$_3$) $\delta$7.98 (d, 3H), 6.88 (d, 2H), 3.76 (s, 3H), 3.30 (t, 2H), 2.76 (t, 2H).

3-(4-Hydroxylbenzoyl)propionic acid (Compound 3.3)

The methoxy derivative, Compound 3.2 (14.54 g, 70 mmol), was dissolved in iodine free hydriodic acid (150 mL) and refluxed at 140° C. for four hours. After the resulting brown solution was cooled to room temperature, water was added and the mixture was neutralized. The aqueous phase was then washed with ether; the organic layers were combined, decolorized, dried and evaporated. The remaining residue was purified by flash silica chromatography to yield a white solid (11.93 g, 88%). $^1$H NMR (CDCl$_3$) $\delta$8.20 (d, 2H), 7.02 (d, 2H), 3.32 (t, 2H), 2.88 (d, 2H).

3-(4-(t-Butyldimethylsiloxyl)benzoyl)propanoic acid (Compound 3.4)

t-Butyldimethylsilyl chloride (0.63 g, 4 mmol) was added a solution of Compound 3.3 (0.23 g, 1 mmol), triethylamine (0.21 g, 20 mmol) and THF (20 mL); this was kept stirred at room temperature for 3 hours. Solvent was then evaporated and the residue was dissolved in ether, washed with dilute HCl and then by saturated bicarbonate. The organic phase was dried and evaporated to yield the disilyl derivative of 3.3. This material could be purified by flash silica chromatography (0.36 g, 78%) and stored, or it could be used immediately. The disilyl compound (0.36 g, 4 mmol) was dissolved in 2-propanol (10 mL) and stirred overnight at room temperature. The solvent was removed by evaporation and replaced with ether. This mixture was then washed with water, dried, evaporated and separated on flash silica chromatography to yield a white solid (0.23 g, 82%). $^1$H NMR (CDCl$_3$) $\delta$7.88 (d, 2H), 6.86 (d, 2H), 3.26 (t, 2H), 2.76 (t, 2H), 0.98 (s, 9H), 0.86 (s, 6H).

4-(4-t-Butyldimethylsiloxyl)phenyl-4-hydroxybutyric acid (Compound 3.5)

A mixture of Compound 3.4 (0.55 g, 2 mmol), NaBH$_4$ (0.04 g, 1 mmol) and methanol (5 mL) was heated to 50°0 C. After 10 hours, the resulting solid was removed by filtration and the solution was evaporated to dryness. The remaining residue was purified on flash silica chromatography to yield a white solid (0.31 g, 56%). $^1$H NMR (CDCl$_3$) $\delta$7.17 (d, 2H), 6.76 (d, 2H), 4.67 (t, 1H), 2.48 (t, 2H), 2.07 (m, 2H), 0.98 (s, 9H), 0.10 (s, 6H).

4-(t-Butyldimethylsiloxyl)phenyl)-4-acetoxybutyric acid (Compound 3.6) (X=acetate)

Acetic anhydride (0.13 g, 1 mmol), triethylamine (0.13 g, 1.2 mmol) and Compound 3.5 (0.22 g, 0.6 mmol) were mixed in CHCl$_3$ for 5 hours at room temperature. The solution was then washed with sodium bicarbonate, dilute HCl and finally dried and evaporated. The remaining residue was purified on flash silica chromatography to yield a solid (0.15 g, 61%). $^1$H NMR (CDCl$_3$) $\delta$7.06 (d, 2H), 6.60 (d, 2H), 5.26 (m, 1H), 2.43 (m, 3H), 2.05 (q, 2H), 0.86 (s, 9H), −0.12 (s, 6H).

Using related chemical techniques derivatives were made in which X=Br (Compound 3.7) internal cyclization prevented further development of this specific approach.

EXAMPLE 5

In order to produce an alkylating agent that is selectively generated in the presence of an ionic strength modifying agent (MX), such as potassium fluoride, the reactive appendage should include a silyloxy group. Related derivatives containing a silyl substitution at a benzyl position are believed to be too stable for the applications described for this invention. Specifically, the characteristics of the —O—Si(R)$_3$ bond, but not a —(R)$_2$C—Si(R')$_3$, are optimal for the controlled alkylation of a target. For example:

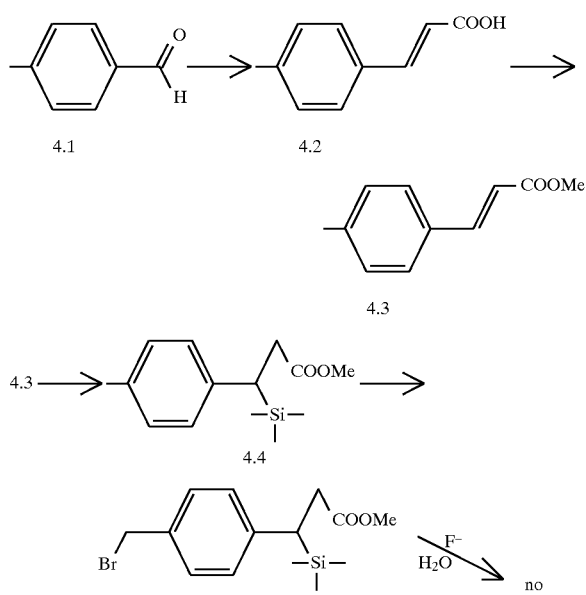

SCHEME 4

These compounds were synthesized and characterized. Compound 4.5 was found to be too stable for use in an aqueous system.

EXAMPLE 6

Synthesis and Characterization of N'-(3-t-[butyldimethylsiloxyl]-4-(p-nitrophenoxy) benzoyl) glycyl-N-hydroxy succinimide Ester This example provides an alternative protocol for the synthesis described above in Example 1. This Example describes a synthetic protocol as well as characterizing data which further refine the protocol and data provided in Example 1. The silyloxy aromatic compound synthesized and characterized as described in this Example, when connected with a sequence-directing oligonucleotide, is a latent site-selective alkylating reagent of DNA. See Examples 1–5.

General Methods. Melting points were measured with a Thomas-Hoover Unimelt apparatus and are uncorrected. The $^1$H NMR and $^{13}$C NMR spectra were measured with a General Electric QE-300 spectrometer and the chemical shifts are relative to the deuterated solvent signal; coupling constants, J, are reported in Hz and refer to apparent peak multiplicities and not true coupling constants. The IR spectra were recorded on a Perkin-Elmer Model 1600 FT-IR spectrophotometer with samples dissolved in CHCl$_3$ in a liquid cell. UV-VIS spectra were recorded on a Perkin-Elmer Lambda 5 spectrophotometer.

Materials. Toluene was distilled over sodium/benzophenone under nitrogen prior to use. HPLC grade acetonitrile was distilled over calcium hydride under nitrogen prior to use. All other chemicals were purchased from Aldrich Chemical Co., Inc.

SCHEME 6

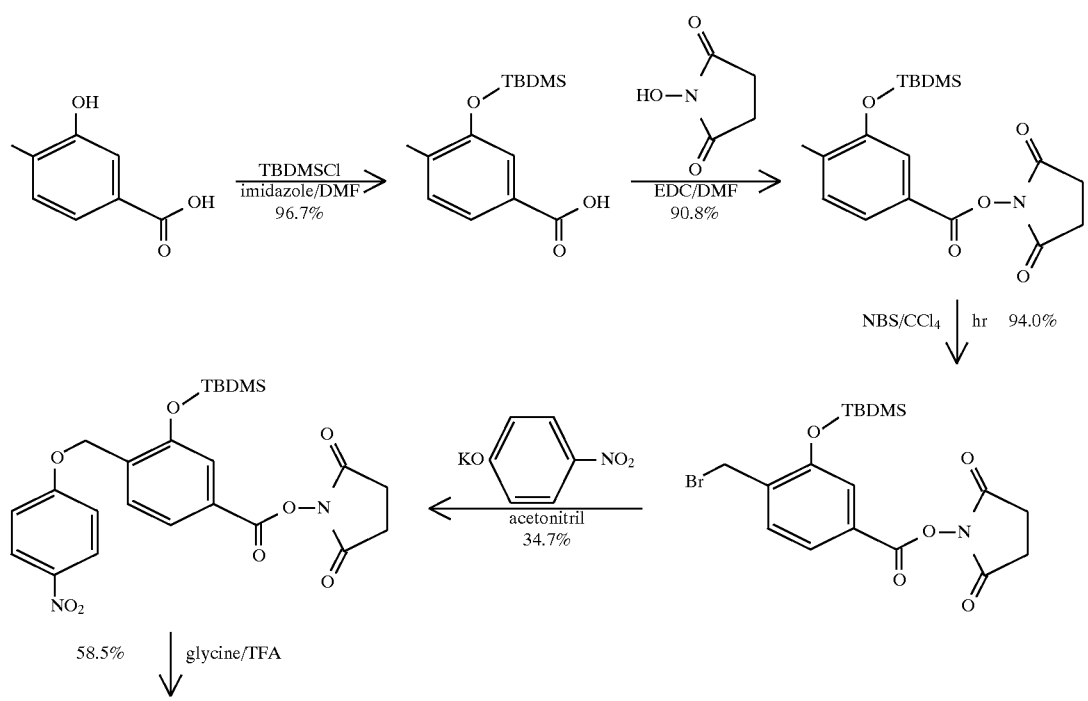

-continued
SCHEME 6

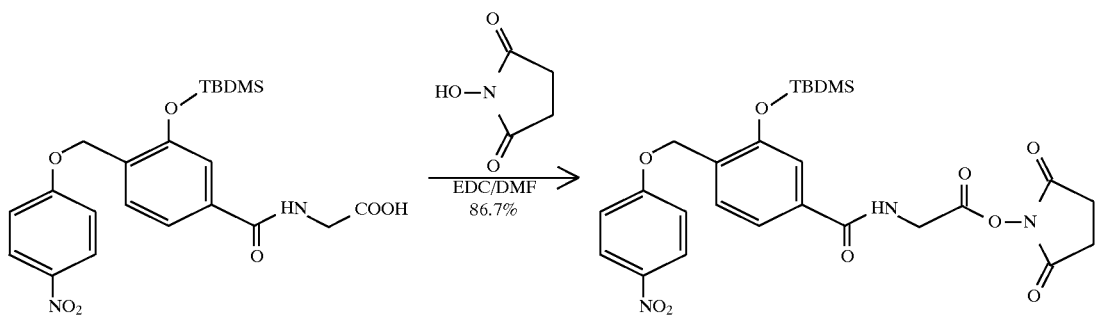

Commercially available 3-hydroxy-4-methyl-benzoic acid (Compound 6.1) was used as starting material. The phenolhydroxy group was protected by TBDMS. The chemical yield of the synthesis of Compound 6.2 was improved by using imidazole as base and DMF as solvent. This method is an alternative to the procedure described above in Example 1 which used trimethylamine as the base and THF as the solvent. Protection and activation of the carboxyl group by N-hydroxy succinimide produced Compound 6.3. Light induced bromination of Compound 6.3 by NBS required a single equivalent of NBS to complete the reaction and to avoid dibromination. Since the solubility of Compound 6.3 is not high in $CCl_4$, some of the product may be lost during filtration to remove the succinimide by-product. Better chemical yield is achieved by chromatographic separation of the reaction mixture without filtration. Chemical yield of the nucleophilic substitution reaction by potassium p-nitrophenolate to produce Compound 6.5 was low. This may be due to the competing attack of the nitrophenolate on the silyl group to desilylate Compound 6.3. Evidence for this was produced insofar as t-butyldimethylsilyl-p-nitrophenol ether was separated out as a by-product. The nitro-phenolate might also attack the activated carboxyl group to form some very polar products that stayed at the original point on TLC. The yield of this step may be further optimized. The subsequent syntheses of Compounds 6.6 and 6.7 were straightforward. The reaction conditions may be further optimized to improve the yield of this step.

3-t-Butyldimethylsiloxyl-4-methyl benzoic acid (Compound 6.2)

3-hydroxy-4-methylbenzoic acid (Compound 6.1) (2.17 g, 14.2 mmol) was dissolved in 30 mL DMF, and then imidazole (4.85 g, 71.0 mmol) and t-butyldimethyl-silyl chloride (6.44 g, 42.6 mmol) were added successively. The reaction mixture was stirred at room temperature (20° C.) for 48 hours. $H_2O$ (50 mL) was added into the reaction mixture and it was extracted by ether. The ether solution was then combined with 2 mL $H_2O$ and one drop of 6N HCl and it was stirred for 48 hours. Then this reaction mixture was washed by $H_2O$, concentrated and subjected to flash silica gel chromatography to yield the product Compound 9.2 (3.67 g, y=96.7%) as a white solid: m.p. 134.5°–135° C.; $^1$H NMR ($CDCl_3$) δ0.26(s,6H), 1.03(s,9H), 2.27(s,3H), 7.22(d, J=7.8 Hz,1H), 7.48(d, J=1.4 Hz,1H), 7.61(dd, J=1.5, 7.8 Hz,1H); $^{13}$C NMR ($CDCl_3$) δ–4.21, 17.19, 18.29, 25.78, 119.64, 123.06, 127.99, 130.95, 135.92, 153.94, 171.82; IR($CHCl_3$) 3600–2600(broad), 2957, 2930, 2859, 1691, 1607, 1577, 1504, 1418, 1273 cm$^{-1}$; UV ($CHCl_3$) $\lambda_{max}$=293 nm; MS(EI) m/z(rel intensity) 266(10.4, M$^{30}$), 209(100).

3-(t-Butyldimethylsiloxyl) 4-methylbenzoyl N-hydroxy-succinimide ester (Compound 6.3)

N-hydroxysuccinimide (1.94 g, 16.8 mmol) was added into a DMF (100 mL) solution of Compound 6.2 (3.00 g, 11.3 mmol) and 1-ethyl-3-(3-dimethylaminopropyl) carbodiimide (EDC) (2.59 g, 13.5 mmol) at 0° C. The mixture was stirred for 20 hours at 4° C. and then it was diluted with brine and extracted with ether. The ether solution was concentrated and the residue was purified by flash silica gel chromatography (Hexane:ethyl acetate=3:1) to yield the product (3.71 g, y=90.8%) as a white solid: m.p. 103.5°–104° C.; $^1$H NMR ($CDCl_3$) δ0.27(s,6H), 1.04(s, 9H), 2.31(s,3H), 2.92(s,4H), 7.28(d, J=7.7 Hz,1H), 7.49(d, J=1.4 Hz,1H), 7.68(dd,J=1.5, 7.8 Hz,1H); $^{13}$C NMR ($CDCl_3$) δ–4.25, 17.27, 18.23, 25.69, 25.85, 119.83, 123.37, 123.59, 131.30, 137.52, 154.21, 161.82, 169.18; IR($CHCl_3$) 3018, 2955, 2931, 2858, 1768, 1741, 1605, 1576, 1503, 1413, 1288, 1210 cm$^{-1}$; UV ($CHCl_3$) $\lambda_{max}$=301 nm; MS(EI) m/z(rel intensity) 363(5.0,M$^+$), 306(38.6), 249(59), 135(100).

3-(t-Butyldimethylsiloxyl)-4-bromomethylbenzoyl N-hydroxysuccinimide ester (Compound 6.4)

N-bromosuccinimide (1.46 g, 8.19 mmol) was added to a solution of Compound 6.3 (2.59 g, 7.12 mmol) in $CCl_4$ (100 mL). The mixture was then maintained at 20° C. and irradiated with a 275 W sunlamp (Sears, #34-7105) for 2 hours over a total period of 4 hours. The irradiation was performed by irradiating in cycles, i.e., irradiating for 10 minutes, followed by 10 minutes to let the lamp cool. After the reaction was completed, $CCl_4$ was removed and the residue was subjected to flash silica gel chromatography (hexane:ethyl acetate=3) to yield the product (2.96 g, y=94.0%) as a white solid: m.p. 155°–155.5° C.; $^1$H NMR ($CDCl_3$), δ0.31(s,6H), 1.04(s,9H), 2.89(s,4H), 4.50(s,2H), 7.45(d,J=7.9 Hz,1H), 7.52(s,1H), 7.69(d,J=7.9 Hz,1H); $^3$C NMR ($CDCl_3$) δ–4.19, 18.22, 25.66, 27.21, 29.52, 119.97, 123.26, 126.23, 131.49, 135.84, 153.98, 161.35, 169.05,; IR ($CHCl_3$) 3018, 2932, 2859, 1772, 1742, 1605, 1575, 1500, 1418, 1291, 1220 cm$^{1}$; MS (EI) m/z(rel intensity) 386(22.0), 384(21.5), 329(22.8), 327(23.3), 272(29.0), 270(28.8), 135 (43.9), 191(42.4), 73(100); MS (FAB,NBA matrix) m/z(rel intensity) 442(M$^+$+1, 0.42), 444(M$^+$+3, 0.33).

3-t(Butyldimethylsiloxyl)-4-(p-nitrophenoxymethyl) benzoyl N-hydroxysuccinimide ester (Compound 6.5)

Potassium p-nitrophenolate (0.158 g, 0.89 mmol) was added to a solution of Compound 6.4 (0.395 g, 0.89 mmol) in freshly distilled acetonitrile (10 mL). The mixture was stirred at room temperature for 1.5 hours and then was concentrated at reduced pressure. The product was isolated from the crude residue by flash silica gel chromatography to give a white solid (0.101 g, y=34.7%): m.p. 56°–57° C., $^1$H NMR (CDCl$_3$) δ0.30(s,6H), 1.01(s,9H), 2.92(s,4H), 5.22(s, 2H), 7.01(dd,J=1.9, 7.3 Hz;1H), 7.54(d,J=7.2 Hz,1H), 7.56 (s,1H), 7.76(d,J=8.0 Hz,1H), 8.23(d,J=7.2 Hz,2H); $^{13}$C NMR (CDCl$_3$) δ−4.23, 18.16, 25.62, 25.65, 65.75, 114.68, 119.85, 123.46, 125.93, 126.08, 129.02, 133.79, 141.98, 153.38, 161.43, 163.23, 168.99; IR (CHCl$_3$) 3018, 2931, 1772, 1742, 1594, 1517, 1420, 1344, 1289, 1261, 1214 cm$^{-1}$; UV(CHCl$_3$) λ$_{max}$=305.8 nm; MS (EI) m/z(rel intensity) 443(0.28), 386(10.26), 328(76.6), 172(48.2), 135 (51.6), 73(100); MS (FAB,NBA matrix) m/z(rel intensity) 501(M$^+$+1,0.22).

N'-(3-t-[Butyldimethylsiloxy]-4-[p-nitrophenoxymethyl]benzoyl)glycine (Compound 6.6)

Triethylamine was added to an aqueous solution (20 mL) of glycine (0.0546 g, 0.728 mmol) to pH=12. This aqueous solution was combined at room temperature with a solution of Compound 6.5 (0.091 g, 0.182 mmol) in acetonitrile (20 mL). The mixture was stirred for 2 minutes and then acidified to pH 2 with 6N HCl and extracted with ether. The combined organic phases were evaporated and the product was purified by flash silica gel chromatography (ethyl acetate:hexane:methanol=8:8:1) to yield a non-crystalline white solid (0.049 g, y=58.5%): $^1$H NMR (CDCl$_3$) δ0.2 7(s,6H), 0.97(s,9H), 4.25(d,J =4.8 Hz,2H), 5.17(s,2H), 6.94–7.00(m,3H), 7.34–7.45(m,3H), 8.20(d,J=9.1 Hz,2H), 10.25(b,1H); $^{13}$C NMR (CDCl$_3$) δ−4.22, 18.19, 25.64, 41.85, 65.84, 114.68, 117.77, 119.34, 125.93, 129.12, 130.44, 134.67, 141.83, 153.70, 163.54, 167.44, 173.30; MS(FAB,NBA matrix) m/z(rel intensity) 461(M$^+$+1,9.72).

N'-(3-t-[butyldimethylsiloxy]-4-(p-nitrophenoxy)benzoyl)glycyl N-hydroxysuccinimide ester (Compound 6.7)

The method described for the synthesis of Compound 6.3 was also used to convert Compound 6.6 to Compound 6.7. N-hydroxysuccinimide (8.3 mg, 0.072 mmol) was added into a DMF (2 mL) solution of 6 (20.0 mg, 0.04 mmol) and EDC (11.5 mg, 0.06 mmol) at 0° C., and the mixture was stirred for 16 hours at 4° C. This was then diluted with brine and extracted with ether. The ether solution was concentrated and the residue was purified by flash silica gel chromatography (hexane:ethyl acetate=3:1) to yield the product (0.021 mg, y=86.7%) as a white solid: m.p. 73°–74.5° C.; $^1$H NMR (CDCl$_3$) δ0.28(s,6H), 0.98(s,9H), 2.85(s,4H), 4.59(d,J=5.5 Hz,2H), 5.18(s,2H), 6.76(t,J=5.4 Hz,1H), 6.99(d,J=9.2 Hz,2H ), 7.34(d,J=7.9 Hz,1H), 7.38(s, 1H), 7.45(d,J=7.9 Hz, 1H), 8.20(d,J=9.2 Hz,2H); $^{13}$C NMR (CDCl$_3$) δ−4.15, 18.21, 25.68, 25.59, 39.54, 65.89, 114.91, 117.88, 119.32, 125.94, 129.14, 130.53, 134.61, 141.91, 153.74, 163.57, 165.91, 166.72, 168.48; IR (CHCl$_3$) : 3018, 2931, 2859, 2360, 1822, 1790, 1744, 1671, 1608, 1593, 1575, 1517, 1497, 1472, 1415, 1372, 1344, 1259, 1218, 1216, 1210 cm$^{-1}$; UV (CHCl$_3$), λ$_{max}$=304 nm; MS (EI) m/z(rel,intensity) 517(1.77), 460(0.25), 436(0.81), 403 (0.91), 386(1.2), 328(49.64), 191(19.29), 135(82.84), 73(100). MS (NH$_3$/DCl, obtained on ZAB 7070 HP) exact mass 575.2173326 (M+NH$_4^+$), calc. 575.2173.

EXAMPLE 7

Synthesis and Characterization of 3-t-butyldimethylsiloxy-4-(p-nitrophenoxy)benzamide

SCHEME 7

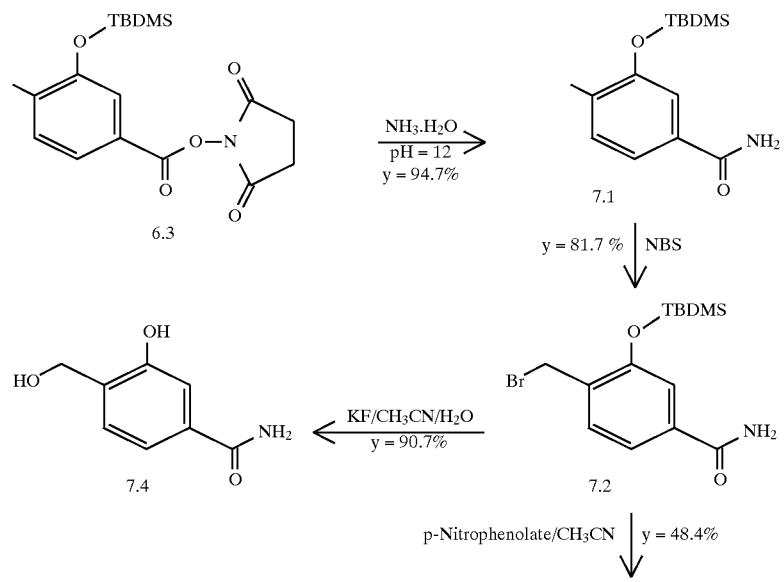

-continued
SCHEME 7

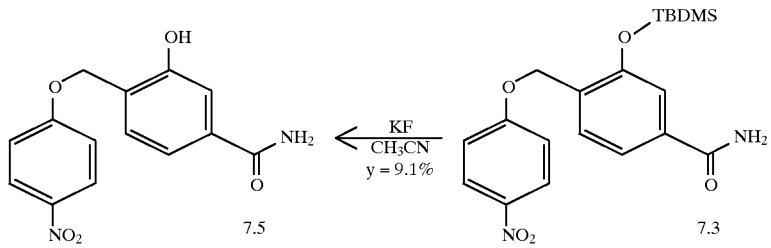

3-t-Butyldimethylsiloxy-4-methylbenzamide (Compound 7.1)

3-t-Butyldimethylsiloxy-4-methylbenzoyl N-hydroxysuccinimide ester (Compound 6.3 synthesized and characterized in Example 6)) (0.206 g, 0.567 mmol) was dissolved in 50 mL of a one to one mixture of acetonitrile and water. Ammonium hydroxide (29%) was added dropwise until the pH=12. After the mixture was stirred for 5 minutes at room temperature, it was acidified with dilute HCl to pH=2. Then ether extraction and flash silica gel chromatography (ethyl acetate:hexane=2:1, Rf=0.5) gave the product as a white solid (0.142 g, y=94.7%). $^1$H NMR (CDCl$_3$) δ0.24(s,6H), 1.02(s,9H), 2.25(s,3H), 5.60(b,1H), 6.05(b,1H), 7.17–7.32 (m,3H); $^{13}$C NMR (CDCl$_3$) δ–4.20, 16.91, 18.22, 25.73, 117.67, 119.57, 130.87, 132.21, 133.61, 154.10, 169.56.

3-t-Butyldimethylsiloxy-4-bromomethylbenzamide (Compound 7.2)

N-Bromosuccinimide (NBS) (0.507 g, 2.85 mmol) was added to a solution of 3-t-butyldimethylsiloxy-4-methyl benzamide (Compound 7.1) in 30 mL CCl$_4$. The mixture was irradiated with a 275 W sunlamp (Sears, #34-7105) at 60° C. Each irradiation took 10 minutes followed by 10 minutes to let the lamp cool down. It took 2 hours of irradiation over a period of 4 hours to complete the reaction. After the solvent was removed at reduced pressure, the residue was subjected to flash silica gel chromatography to yield the product as a white solid (0146 g, y=81.7%). $^1$H NMR (CDCl$_3$) δ0.318(s,6H), 1.05(s,9H), 4.51(s,2H), 6.10 (b,2H), 7.25(d,J=7.8 Hz,1H), 7.32(s,1H), 7.39(d,J=7.9 Hz,1H); $^{13}$C NMR (CDCl$_3$) δ–4.08, 18.28, 25.76, 27.87, 117.99, 118.07, 119.49, 131.23, 132.54, 134.97, 168.46.

3-t-(Butyldimethylsiloxy)-4-(p-nitrophenoxymethyl) benzamide (Compound 7.3)

Potassium p-nitro-phenolate (0.252 g, 142 mmol) was added to a solution of Compound 7.2 (0.49 g, 1.42 mmol) in freshly distilled acetonitrile (10 mL). The mixture was stirred at room temperature for 22 hours. After the solvent was removed at reduced pressure, the residue was absorbed on 2 g silica gel, then it was subjected to flash chromatography to give the product as a white solid (0.282 g, y=48.4%). $^1$H NMR (CDCl$_3$) δ0.291(s,6H), 0.99(s,9H), 5.18(s,2H), 6.10(b,2H), 7.00(dd,J=2.1, 7.2 Hz,2H), 7.33 (d,J=7.8 Hz,1H), 7.38(s,1H), 7.45(d,J=7.8 Hz,1H), 8.20 (dd,J=2.1, 7.2 Hz,2H); $^{13}$C NMR (CDCl$_3$) δ–4.16, 18.21, 25.65, 65.86, 114.68, 117.94, 119.62, 125.95, 129.03, 130.32, 134.76, 141.80, 153.64, 163.56. 168.67.

3-Hydroxy-4-hydroxymethylbenzamide (Compound 7.4)

To the solution of 3-t-butyldimethylsiloxy-4-bromomethylbenzamide (Compound 7.2) (0.101 g, 0.293, mmol) in 8 mL CH$_3$CN, KF.2H$_2$O (0.041 g, 0.44 mmol) in 4 mL H$_2$O was added dropwise. The mixture was then stirred at room temperature for half hour. After the solvent was removed, the residue was absorbed on 500 mg silica gel. The product was obtained by flash chromatography (ethyl acetate:ethyl alcohol=10:1, Rf=0.8) as a white solid (0.0439 g, y==90.7%). $^1$H NMR (CD$_3$CN) δ4.68(s,2H), 5.95(b,1H), 6.69(b,1H), 7.23–7.26(m,3H), 7.77(b,1H); $^{13}$C NMR (CD$_3$Cl) δ60.66, 115.13, 119.44, 128.69, 133.07, 134.94, 156.10, 203.64.

3-Hydroxy-4-(p-nitrophenoxymethyl)benzamide (Compound 7.5)

KF.2H$_2$O (0.0034 g, 0.12 mmol) was added to an acetonitrile (10 mL) solution of 3-(t-butyldimethylsiloxyl)-4-(p-nitrophenoxymethyl)benzamide (Compound 7.3) (9.8 mg, 0.024 mmol), the mixture was stirred for one hour at room temperature. The acetonitrile was removed at reduced pressure. The residue which was yellow solid was partly dissolved in acetonitrile and this acetonitrile solution was subjected to a flash silica gel chromatography (ethyl acetate:hexane=2:1, Rf=0.12) to yield a white solid (0.6 mg, y=9,1%): $^1$H NMR (CD$_3$CN) δ5.24(3,2H), 6.00(b,1H), 6.75 (b,1H), 7.14(d,J=0.2 Hz,2H), 7.30–7.33(m,3H), 7.44(d,J= 7.8 Hz, 1H), 7.62(b,1H), 8.20(d,J=9.2 Hz,2H).

EXAMPLE 8
Analysis of Solvolysis of a Model Compound by $^1$H NMR

The complexity of the conjugate system renders the study of in vitro alkylation processes by $^1$H NMR difficult. Therefore a model compound (Compound 7.3 of Example 7) was synthesized which is structurally similar to the functional moiety of the conjugate. The solvolysis of the model compound induced by the fluoride ion proceeded in two stages as shown in Scheme 8.

SCHEME 8

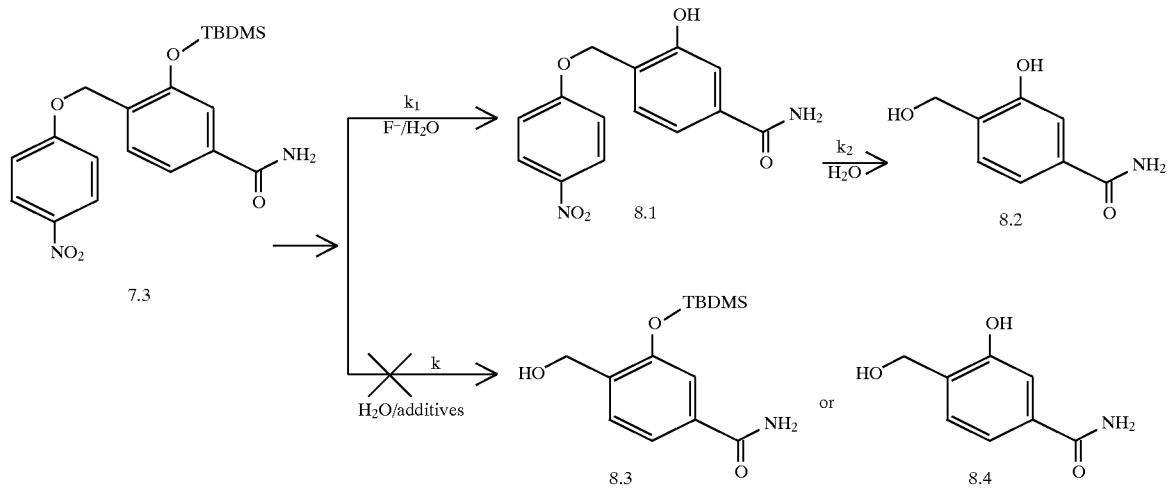

additives = LiClO$_4$, or nucleoside dG

General Procedure for the NMR study: 429 μL of the model compound, 3-t-butyldimethylsiloxy-4-(p-nitrophenoxymethyl)benzamide (Compound 7.3) (4 mM in CD$_3$CN), and 71 μL of 2-[N-morpholino]ethanesulfonic acid in sodium deuteroxide (MES-NaOD) buffer (70 mM, pD=6.5) were mixed in a NMR tube. The $^1$H NMR spectrum was recorded. Then 10 μL of KF (200 mM in D$_2$O) or LiClO$_4$ (250 mM or 5M) was added into the system. The proton NMR spectra were recorded with the increase of time at room temperature (20=0.5° C.). For the deprotection step, the percentages of the starting material at different times were calculated based on the fact that the sum of the integrations of the methylene protons peaks, δ5.21 for the starting material and 5.16 for the deprotection product, were unchanged when compared to peak of MES which was used as an internal standard. In a similar way, for the second stage, we used the proton peaks of the p-nitrophenoxy group as the key peaks. This method is more sensitive to integration for calculating the percentage of the solvolysis product.

The first stage of solvolysis is the deprotection of the phenol hydroxy group on the model compound (Compound 7.3) by fluoride ion to form Compound 8.1. From proton NMR, it was observed that the decrease of the methylene proton peak of the starting material and the increase of the methylene proton peak of the product are complete in about twenty minutes. Using the integration of the methylene proton peaks, the percentage of the starting material remaining was calculated based on the assumption that the sum of the starting material and the product was equal to 100%.

Figure 4:
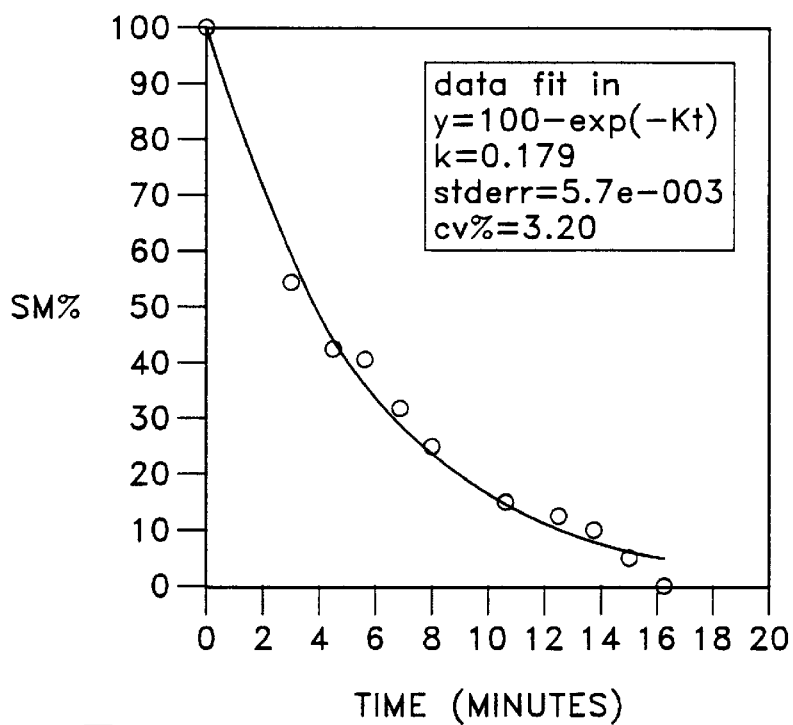
FIG. 4 illustrates proton NMR data concerning the fluoride-mediated deprotection of a silyloxy aromatic compound of the present invention (starting material=SM), as described in Example 8. Conditions: MES-NaOH buffer (70 mM, pD=6.5), 71 µL; SM (4 mM, $CD_3CN$), 429 µL; KF (200 mM, $D_2O$), 10 µL.

As shown in FIG. 4, this step proceeds as a first order reaction with a time constant of 0.178 min$^{-1}$. It was observed that 50% conversion of the starting material (model compound) to product (Compound 8.1) took more than 200 hours. The methylene proton peak of the final product was observed at δ4.60 ppm.

Figure 5:
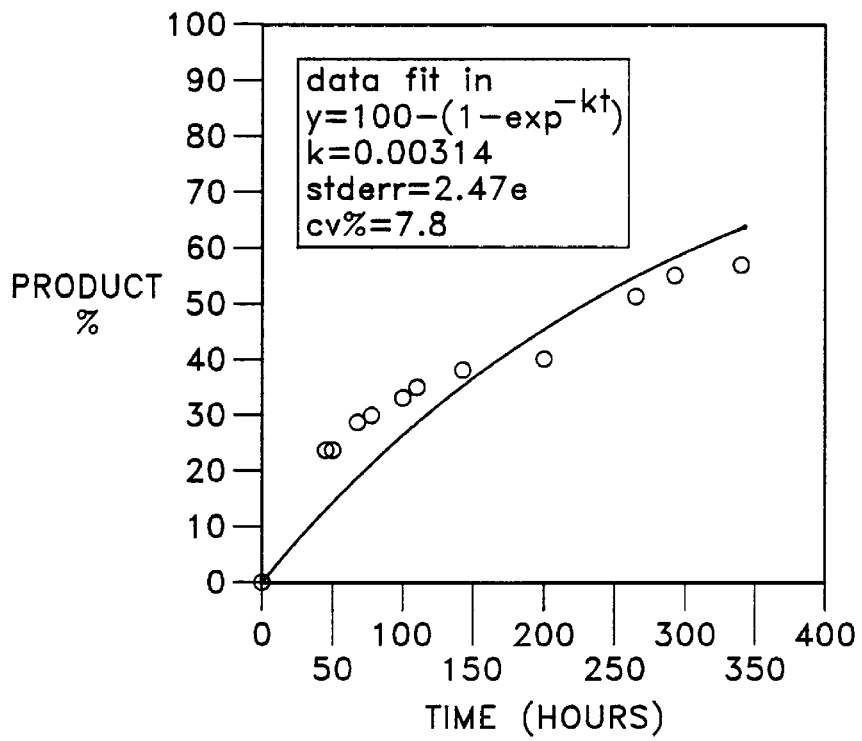
FIG. 5 illustrates proton NMR data concerning production of para-nitrophenol as an indicator of hydrolysis of a deprotected silyloxy aromatic compound of the present invention, as discussed in Example 8. Conditions: MES-NaOH buffer (70 mM, pD=6.5), 71 µL; SM (4 mM, $CD_3CN$), 429 µL; KF (200 mM, $D_2O$), 10 µL.

In the second stage, para-nitrophenol formed as a side product, and the integration of the peaks for this compound were more convenient to measure. In this case the two doublets of the para-nitrophenol at δ6.85 ppm and 8.05 ppm were used to calculate the formation of the product (Compound 8.2). FIG. 5 shows the formation of the product increasing with time with first order reaction rate constant of 0.00314 hour$^{-1}$.

In the presence of LiClO$_4$ the reaction system was kept in an NMR tube at 20° C. for ten days without any obvious change in the $^1$H NMR. This implies that LiClO$_4$ cannot promote the solvolysis of the model compound either by deprotection of the phenolhydroxy group or by promotion of the nucleophilic substitution at the benzylic position by water directly.

$^1$H NMR monitoring did not reveal any o-quinone methide intermediate formation in the fluoride-induced solvolysis. However, the o-quinone methide intermediate may be involved in the solvolysis process if, after the deprotection stage, the formation of the o-quinone methide is the rate-determining step. In such a case, once the highly reactive intermediate is formed, it is captured instantly by the solvent to form the final solvolysis product. It is assumed that this reaction is so fast that it is not observable by NMR techniques. Nevertheless, from the NMR study, it is known that the fluoride ion is the only ion capable of deprotecting the phenolhydroxy group and thereby promoting further solvolysis. LiClO$_4$ was not observed to promote solvolysis, but did promote the alkylation and cross-link in the in vitro experiments. Because of the limited conditions necessary for proton NMR studies, additional experiments (Example 9) were performed using conditions closer to those used in the initial in vitro experiments described in Examples 1–5.

EXAMPLE 9

Kinetic Analysis of the Solvolysis of the Model Compound by UV-VIS Spectroscopy

UV-VIS spectroscopy was used to investigate the reaction in the presence of fluoride ion, non-fluoride salts, and nucleoside. The reaction was studied by monitoring the formation of para-nitrophenol which has an absorption maximum at 400 nm.

General procedure for the UV-VIS spectroscopy study: The model compound, buffer solution and additives (KF, non-fluoride salts, or nucleoside dG) were combined in a 1 mL cuvette, and maintained at 20° C. The visible absorbance at 400 nm was recorded with time automatically.

Figure 6:
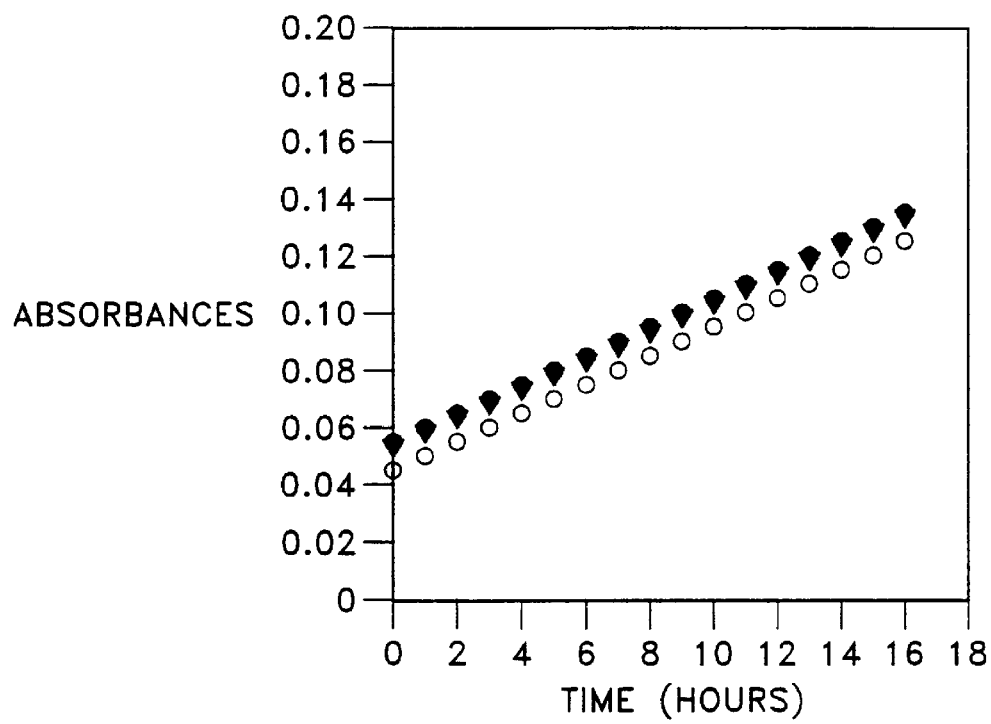
FIG. 6 illustrates spectrophotometric data showing that a large excess of fluoride does not influence the second stage (hydrolysis) of deprotection of a silyloxy aromatic compound of the invention, as described in Example 9. Conditions: final concentration [SM]=0.04 mM, MES-NaOH buffer (pH=7) 40 mM, Org./Ag.=3:7; KF=(○) 2 mM, (●) 10 mM, (▽) 20 mM, (▼) 25 mM.

FIG. 6 demonstrates that a large excess of potassium fluoride does not further promote solvolysis of the model compound, implying that potassium fluoride has no effect on the second stage of solvolysis.

SCHEME 9

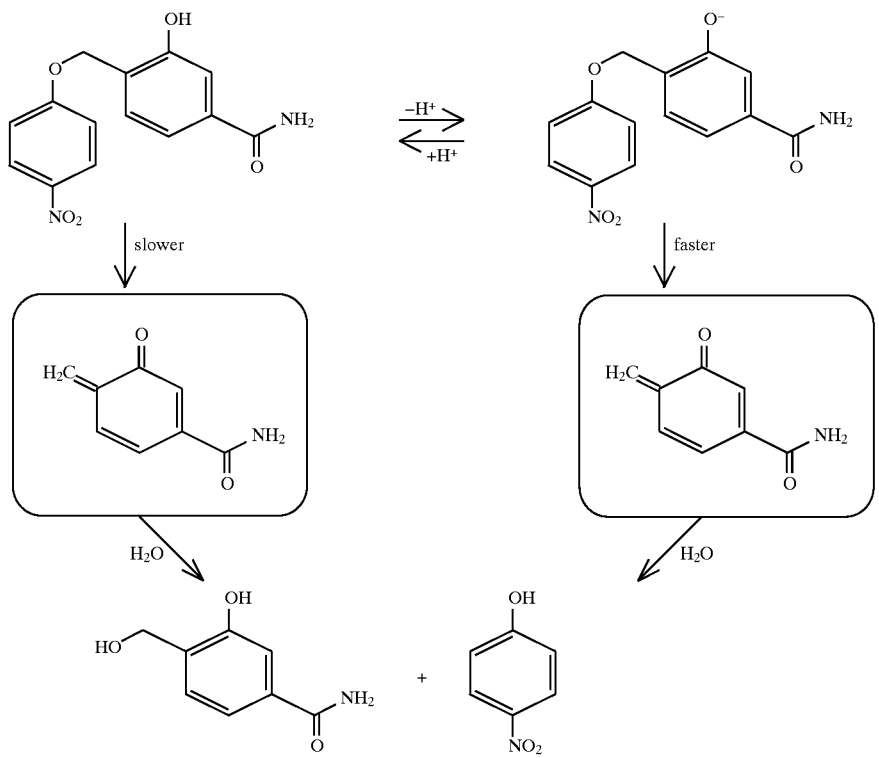

Figure 7:
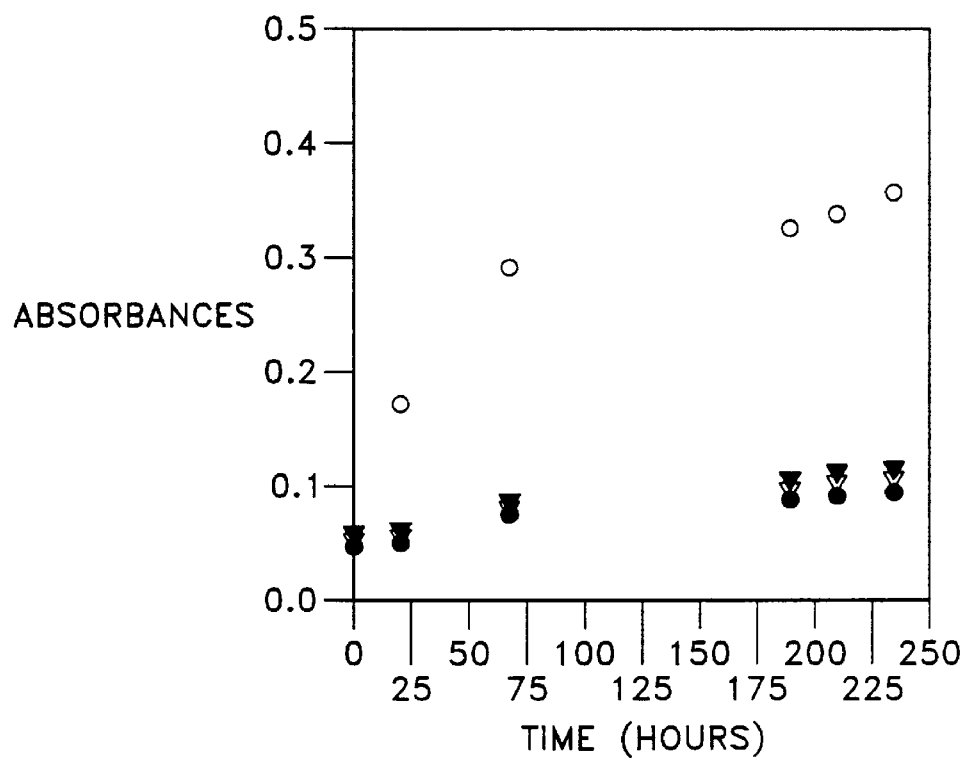
FIG. 7 illustrates spectrophotometric data showing that the second stage of solvolysis of a silyloxy aromatic compound of the invention is not mediated by non-fluoride salts, as described in Example 9. Conditions: final concentration [SM]=0.04 mM, MES-NaOH buffer (pH=7) 40 mM, org./ag.=3:7; (○) [KF]=10 mM, (●) [KBr]=250 mM, (▽) [$LiClO_4$]=250 mM, (▼) [NaCl]=250 mM.

FIG. 7 shows that in the presence of non-fluoride salts, the formation of para-nitrophenol is so slow as to be negligible. This is consistent with the proton NMR study results shown in Example 8.

Figure 8:
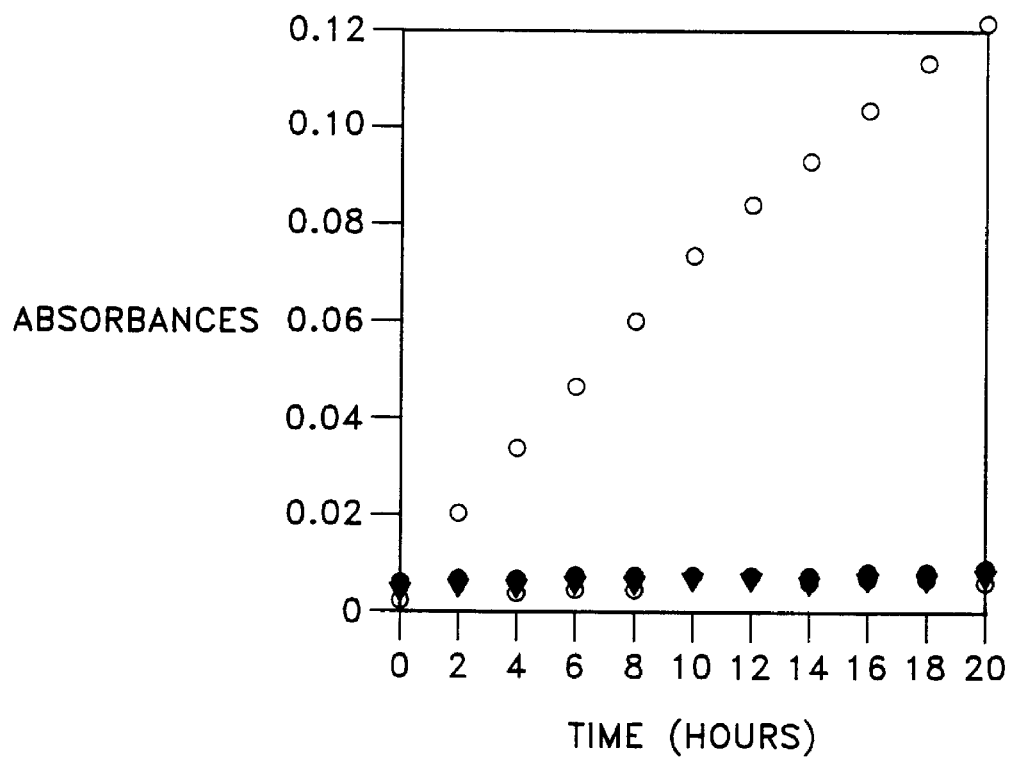
FIG. 8 illustrates spectrophotometric data showing that a nucleoside, deoxyguanine (dG), in either the presence or absence of $LiClO_4$, does not promote solvolysis of a silyloxy aromatic compound of the invention, as described in Example 9. Conditions: final concentration [SM]=0.04 mM, MES-NaOH buffer (pH=7) 40 mM, org./ag.=3:7; (○) [KF]=10 mM, (●) [dG]=0.71 mM, (▽) [dG]=0.71 mM+[$LiClO_4$]=250 mM, (●) [$LiClO_4$]=250 mM.

FIG. 8 shows that the effect of a nucleoside, deoxyguanine (dG), either in the presence or the absence of $LiClO_4$, does not promote the nucleophilic substitution of the para-nitrophenol and does not help the solvolysis.

In summary, the model compound showed solvolysis reactivity only when the phenolhydroxy group was deprotected by fluoride ion. Without deprotection, the model compound is apparently quite stable in the environment of nucleophiles such as water or nucleoside. Non-fluoride salts were not found to enable or promote any type of nucleophilic substitution at the benzylic position of the model compound. Combining these kinetic model study results with the in vitro experimental results, it is reasonable to propose that the alkylation of the target DNA by the conjugate is induced by fluoride ion via o-quinone methide intermediate formation. In the presence of non-fluoride salts, however, it is the target DNA itself which promotes the alkylation by hybridization with the conjugate to form a conformational microenvironment in which the proximity between the bases on target DNA and the functional group on the conjugate is increased.

EXAMPLE 10

Additional kinds of latent bifunctional DNA alkylating agents are possible, which spontaneously decompose, alkylate, and ultimately cross-link duplex DNA without the aid of extracellular or intracellular activation. In this example, a series of compounds is illustrated which have the inducible activity of forming two reactive electophilic centers as quinone methide intermediates and capable of cross-linking DNA as shown in Scheme 10. The positions of the two methylene groups on the aromatic ring systems may be adjusted to correspondingly adjust the distance between the latent electrophile centers. This adjustment enables the achievement of site specific cross-linking of duplex DNA.

SCHEME 10

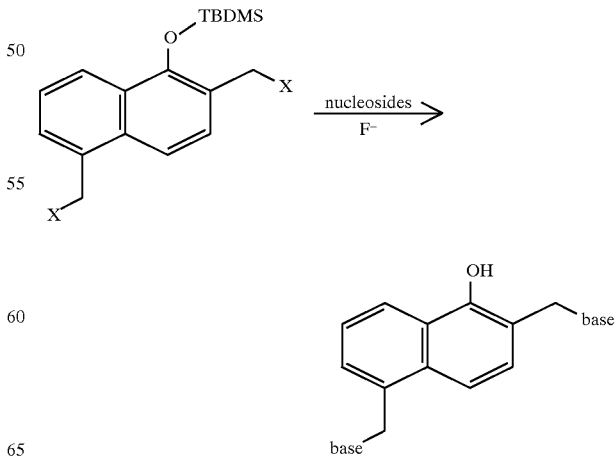

SCHEME 10 -continued

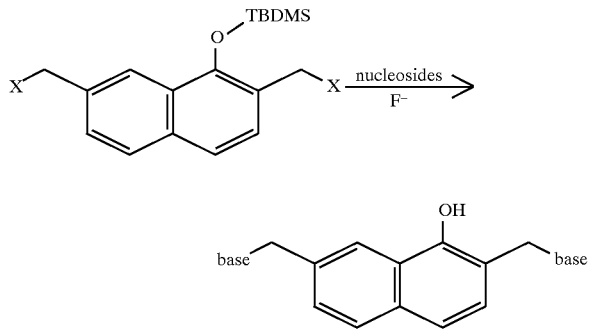

The synthesis of the bifunctional compounds is illustrated in Scheme 10. In this scheme, the Friedel-Craft reaction was straightforward and the yield was high. Proton NMR of the product mixture showed that 2,7-dimethyl-α-tetralone was the major product. Aromatization of the dimethyl tetralones by bromination, followed with refluxing in base gives dimethyl-α-naphthols as a white solid. The major product, 2,7-dimethyl-α-naphthol, was obtained as a pure crystalline solid via recrystallization from hexane. The protection of the hydroxy group by t-butyl dimethyl silyl chloride was straightforward with quantitative yield. Bromination of the protected 2,7-dimethyl-α-naphthol with N-bromosuccinimide was successful, although the reaction and purification conditions may be further optimized.

SCHEME 11

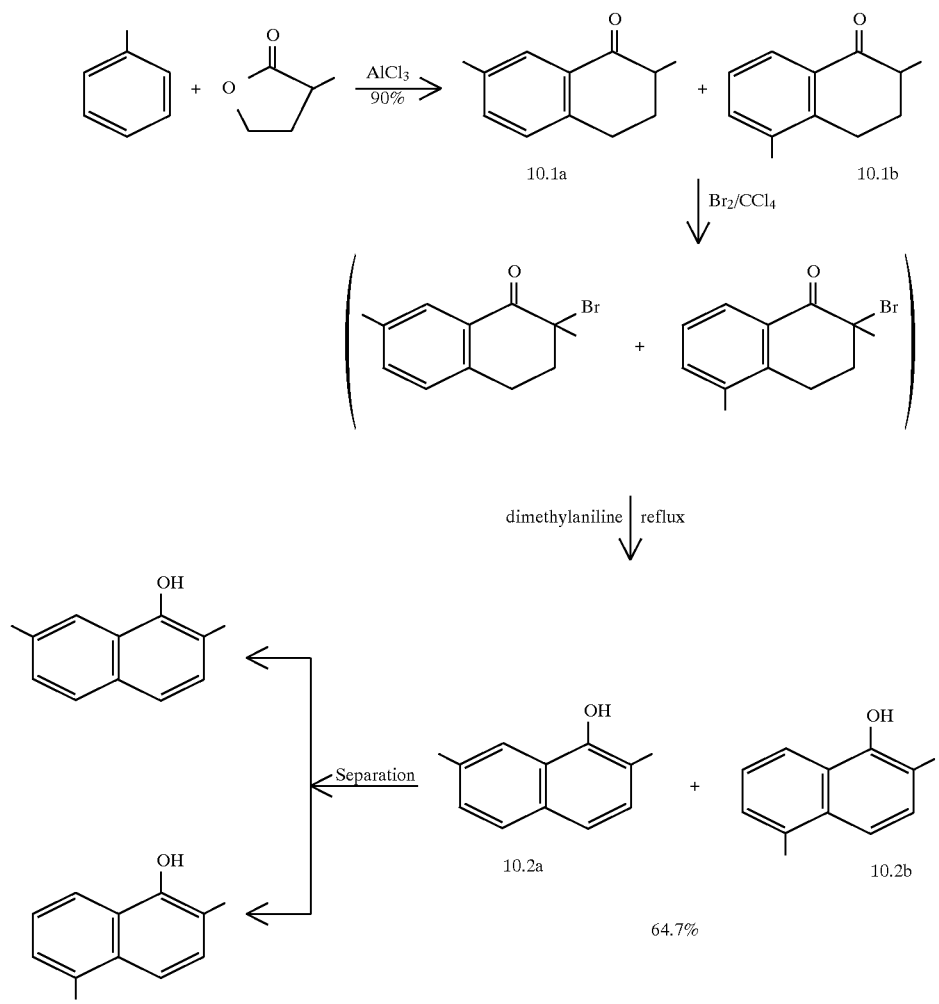

-continued
SCHEME 11

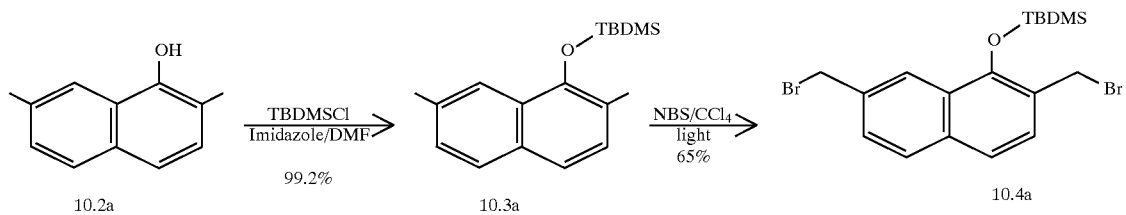

2,7-Dimethyl-α-tetralone (Compound 10.1a) and 2, 5-dimethyl-α-tetralone (Compound 10.1b)

AlCl₃ (60.0 g, 0.45 mol) was added to a freshly distilled dry toluene (200 mL) solution of α-methyl-λ-butyrolactone (10.48 g, 0.10 mol) over a period of 15 minutes. The reaction mixture was then stirred at 100° C. for 30 minutes, and next at 80° C. for 15 hours. It was then cooled to room temperature and poured onto 500 g crushed ice, drenched with 500 mL of concentrated hydrochloric acid. The lower aqueous layer was separated and extracted with about 500 mL toluene. The brown organic, upper layer and the toluene extract were combined, washed successively with water, 20% potassium hydroxide solution, and water, and distilled under reduced pressure to remove toluene and traces of water. Distillation of the residue yielded (16.2 g, y=90%) dimethyl-α-tetralones: b.p. 130°–135° C./1 mm Hg.

Aromatization of the dimethyl-α-tetralones: A solution of bromine (42.35 g, 0.26 mol) in 100 mL carbon disulfide (CS₂) was added dropwise to a stirred solution of dimethyl-α-tetralones (38.43 g, 0.22 mol) in 200 mL CS₂ at 0° C. After stirring for an additional 3.5 hours at 4° C., the solvent and the excess of bromine were removed at reduced pressure at room temperature, leaving a thick dark brown oil. To this oil, 70 mL freshly distilled N,N-dimethylaniline was added and the solution was refluxed for 3.5 hours under nitrogen. After it was cooled down, the mixture was acidified with dilute sulfuric acid and extracted with ether. After the ethereal solution was washed with 10% sodium acetate solution and with water, it was extracted with 10% aqueous NaOH solution. The alkaline solution was then acidified with dilute sulfuric acid and extracted with ether. The ethereal solution was washed with water and dried with MgSO₄. After removing the ether at reduced pressure, the residue was subjected to silica gel chromatography using pure hexane as eluant. A mixture of 2,7-dimethyl-α-naphthol (Compound 10.2a) as major product and 2,5-dimethyl-α-naphthol (Compound 10.2b) as minor product was obtained as a white solid (24.58 g, y=64.7%). Pure 2,7-dimethyl-α-naphthol was obtained as a crystalline solid by recrystallization in hexane: m.p. 124°–125° C.; ¹H NMR (CDCl₃) δ2.40(s,3H), 2.50(s,3H), 5.08(b,1H), 7.21(d,J=8.4 Hz,1H), 7.29–7.33(m,2H), 7.56(s,1H), 8.02(d,J=8.5 Hz,1H); ¹³C NMR (CDCl₃) δ15.44, 21.57, 115.48, 119.60, 120.68, 122.63, 126.70, 127.53, 129.02, 133.81, 134.90, 148.58; IR(CHCl₃) 3605, 3055, 2922, 1575, 1507, 1379, 1268, 1248, 1218, 1211 cm⁻¹; MS(EI) m/z(rel intensity) 172(M⁺,100), 157(25.2), 129(38.9), 128(42.9).

t-Butyldimethylsilyl-2,7-dimethyl-α-naphthol ether (Compound 10.3a)

2,7-dimethyl-α-naphthol (Compound 10.2a)(2.02 g, 11.8 mmol) was dissolved in 20 mL DMF, imidazole (4.01 g, 58.9 mmol) and t-butyldimethyl chloride (4.44 g, 29.4 mmol) were then added successively. The reaction mixture was stirred at room temperature (20° C.) for 32 hours. Brine (50 mL) was added into the reaction mixture and it was extracted by ether. The ethereal solution was washed several times with brine and dried with MgSO₄. After removing the ether, the residue was subjected to silica gel chromatography (hexane:ethyl acetate=120:1) to yield a colorless oil as product: ¹H NMR (CDCl₃) δ0.205(s,6H), 1.16(s,9H), 2.39 (s,3H), 2.51(s,3H), 7.24–7.29(m,2H), 7.36(d,J=8.3 Hz,1H), 7.55(s,1H), 7.97(d,J=8.6 Hz,1H); ¹³C NMR (CDCl₃) δ–3.10, 17.41, 18.79, 21.40, 26.20, 120.68, 122.00, 122.73, 126.50, 126.58, 126.96, 129.61, 133.97, 134.41, 148.60; IR (CHCl₃) 3010, 2954, 2930, 2860, 1592, 1565, 1498, 1473, 1410, 1355, 1260; MS(EI) m/z(rel intensity) 28 6(M⁺,20.7), 229(100), 214(36.1), 199(31.8).

t-Butyldimethylsilyl-2,7-dibromomethylene-α-naphthol ether (Compound 10.4a)

N-Bromosuccinimide (0.874 g, 4.91 mmol) was added to a solution of t-butyldimethyl-silyl-2,7-dimethyl-α-naphthol (Compound 10.3a) (0.638 g, 2.33 mmol) in 25 mL CCl₄. The mixture was irradiated with a 275 W sunlamp (Sears, #34,7105). Each irradiation took 10 minutes, followed by 10 minutes to let the lamp cool down. It took 4 hours over a total period of 8 hours to complete the reaction. After the by-product succinimide was filtered out and the solvent was removed at reduced pressure, the residue was subjected to a silica gel column which was prerunned with 5 drops of triethylamine and 250 mL hexane. The product obtained was a yellowish oil which contained small quantities of over-brominated products (0.645 g, y=65%). A small amount of pure sample was obtained by doing silica gel chromatography again. ¹H NMR (CDCl₃) δ0.22(s,6H), 1.14(s,9H), 4.63 (s,2H), 4.67(s,2H), 7.54(d,J=8.7 Hz,1H), 7.79(s,1H), 8.08 (d,J=8.7 Hz,1H) 8.12(m,2H), ¹³C NMR (CDCl₃) δ–3.28, 18.78, 26.02, 28.40, 33.14, 115.09, 124.58, 124.94, 127.02, 127.20, 128.87, 132.53, 132.86, 137.48, 148.86,; IR (CHCl₃) 2931, 1558, 1540, 1506, 1472, 1410, 1355, 1259, 1218, 1213 cm⁻¹; MS (EI) m/z(rel intensity) 441(M⁺,2.1), 443(M⁺+2,4.0), 445(M⁺+4,1.2), 73(100).

EXAMPLE 11

Experimental Procedure

SCHEME 12

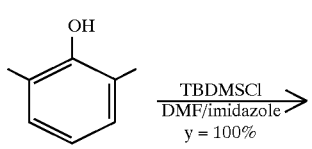

-continued
SCHEME 12

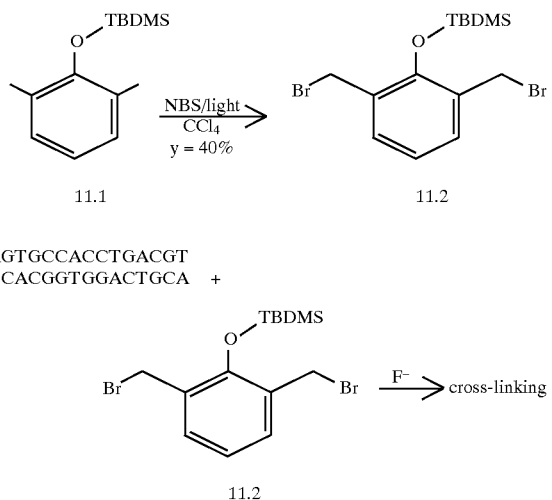

t-Butyldimethylsilyl-2,6-dimethylphenol ether (Compound 11.1)

2,6-Dimethylphenol (0.452 g, 3.7 mmol) was dissolved in 10 ml DMF, and to this imidazole (1.00 g, 14,9 mmol) and t-butyldimethyl chloride (1.12 g, 7.4 mmol) were then added successively. The reaction mixture was stirred at room temperature (20° C.) for 12 hours. Brine (30 ml) was added and the mixture was extracted by ether (4×30 ml). The ethereal solution was washed several times with brine and dried over $MgSO_4$. After removing the ether, the residue was subjected to flash silica gel chromatography (hexane:ethyl acetate=120:1) to yield a colorless oil as product (0.873 g, y=100%): $^1$H NMR ($CDCl_3$) δ0.20 (s, 6H), 1.50 (s, 9H) 2.22 (s, 6H), 6.82 (t, 1H), 7.05 (d,2H).

t-Butyldimethylsilyl-2,6-di(bromomethyl)phenol ether (Compound 11.2)

N-Bromosuccinimide (0.337 g, 1.89 mmol) was added to a solution of t-butyldimethylsilyl-2,6-dimethyl phenol ether (0.224 g, 0.95 mmol) in 20 ml $CCl_4$. The mixture was irradiated with a 275 W sunlamp (Sears, #34-7105) for a total of 160 min. The lamp was alternatively switched on and off every 10 min. Afterward, the by-product succinimide was removed by filtration and the solvent was removed at reduced pressure. The remaining residue was subjected to silica gel chromatography (hexane:ethyl acetate=3:2) to yield a colorless oil (0.150 g, y=40%): $^1$H NMR ($CDCl_3$) δ0.30 (s, 6H), 1.10 (s,9H), 4.50 (s, 4H), 6.98 (t, 1H), 7.38 (d, 1H).

Radiolabeling of DNA

The deoxyoligonucleotide d(AGTGCCACCTGAGGT) (0.05 O.D., ca. 0.3 nmol of bases) was treated with γ-$^{32}$P-ATP (5.0 μL, 50 μCi, specific activity of 3000 Ci/mmol), $T_4$ kinase buffer (1.5 μL of 0.05M TrisHCl, pH=7.6, 0.01M $MgCl_2$, 5 mM DTT, 0.1 mM EDTA and 0.1 mM spermidine) and $T_4$ polynucleotide kinase (1 μL, 10 units) for 30 min. at 37° C. The reaction mixture was diluted to 2 ml with deionized water and centrifuged in a concentrator (Amicon, 10,000 MW cutoff) for 40 min. at 4° C. (8000 rpm) to remove the excess salt and unincorporated γ-$^{32}$P-ATP. Subsequently an additional 1.5 ml water was added to the tube and the last step was repeated. The process provided about 8.8 μCi of phosphorylated 5'-radiolabeled oligonucleotide.

DNA cross-linking

Figure 9:
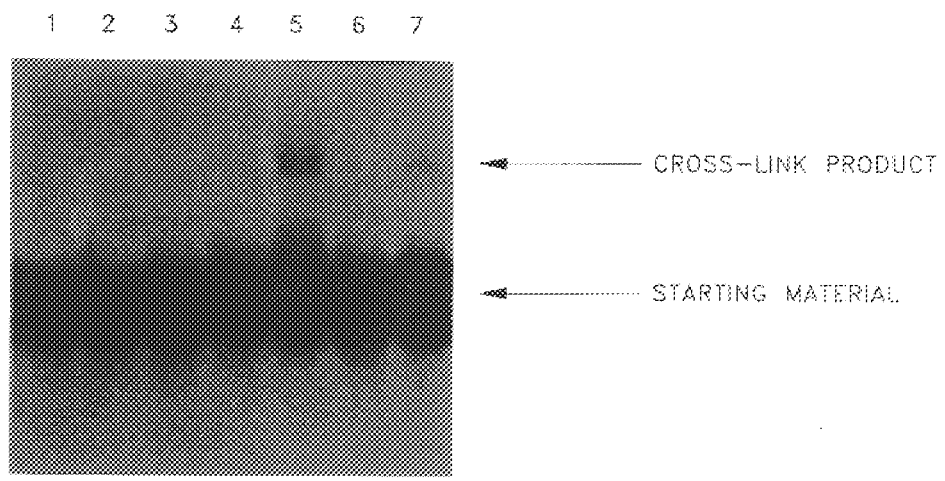
FIG. 9 shows an autoradiogram of denaturing polyacrylamide gel (20%) used to identify the cross-link product of duplex DNA by t-butyldimethyl-2,5-dibromomethylenephenol ether (Compound 11.2) as described in Example 11.

The double helix DNA solution was prepared prior to the reaction, 5'-$^{32}$P-Radiolabeled d(AGTGCCACCTGAGGT) (40 μL, 0.001 O.D., ca. 6 pmol, 176 nCi), unlabeled d(AGTGCCACCTGACGT) and its fully complementary strand d(ACGTCAGGTGGCACT) (5 μL, 0.086 O.D.), 20 μL MES-NaOH buffer (10 mM, pH=7.0) and 40 μL $H_2O$ were placed in a microfuge tube. The tube was heated in water bath to 85° C. and the bath and tube were allowed to cool down to room temperature. Typically, 5 μL of the above solution was mixed with 3 μL of an ethanol solution of t-butyldimethylsilyl-2,6-di(bromomethyl) phenol ether (5 mM) in a microfuge tube. After the mixing and preincubation (various times as shown in FIG. 9), 2 μL of KF (50 mM) in water was added and it was incubated at 37° C. for 12 hours. The reaction mixture was then dried by speed-vac and analyzed by denaturing PAGE (20%, 7M urea) and autoradiography.

FIG. 9 shows an autoradiogram of denaturing polyacrylamide gel (20%) used to identify the cross-link product of duplex DNA by t-butyldimethyl-2,5-dibromomethylenephenol ether (Compound 11.2). Lane 1: duplex DNA(3 μM)+KF(10 mM): Lane 2: duplex DNA(3 μM) alone: Lane 3: duplex DNA(3 μM)+Compound 11.2 (1.5 mM); Lane 4: duplex DNA(3 μM)+Compound 11.2 (1.5 mM), 12 hours pre-incubation at 25° C., addition of KF (10 mM), 30 min. incubation at 37° C.; Lane 5: duplex DNA(3 μM)+Compound 11.2 (1.5 mM), no pre-incubation, addition of KF (10 mM), 12 hours incubation at 37° C.; Lane 6: duplex DNA (3 μM)+Compound 11.2 (1.5 mM), 12 hours pre-incubation at 25° C., addition of KF (10 mM), 30 min. incubation at 25° C.; Lane 7: duplex DNA (3 μM)+ Compound 11.2 (1.5 mM), no pre-incubation, addition of KF (10 mM), 12 hours incubation at 25° C.

EXAMPLE 12

DNA Cross-Linking Assay 5'-$^{32}$P-Radiolabeled (ca. 6 pmol, 176 nCi) and unlabeled $D_c$ d(AGTGCCACCTGACGT) (ca. 0.6 nmol) and its complementary strand $D_1$ d(ACGTCAGGTGGCACT) (ca. 0.6 nmol) was annealed in MES-NaOH buffer (2 mM, 100 μL) in a microfuge tube. The tube was heated in a water bath to 90° C. and the bath with the tube were allowed to cool to room temperature in about 2 hours. Typically, 5 μL of the above solution was mixed with 3 μL of a 1.5 mM solution of one of four different silyloxy aromatic alkylating agents in aqueous acetonitrile (7:3). The four agents used in this experiment were:

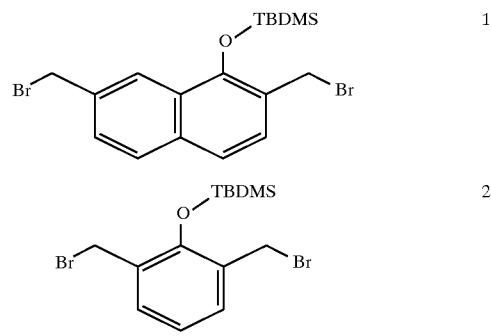

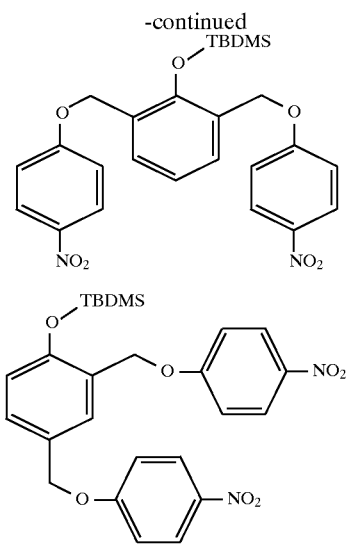

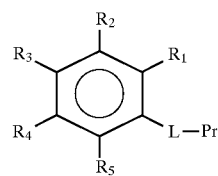

Figure 10:
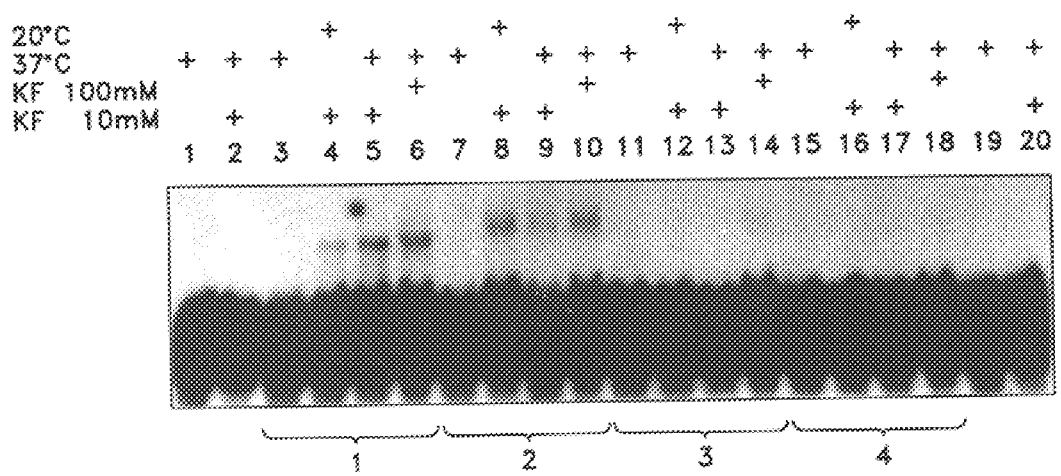
FIG. 10 shows an autoradiogram of denaturing polyacrylamide gel (20%) used to identify cross-linked products of DNA by four different silyloxy aromatic agents of the invention.

Reactions were initiated by addition of 2 μL aqueous KF (10 or 100 mM final concentration). The mixtures were incubated at 20° or 37° C. for 24 hours, then dialyzed against water for 12 hours, dried by speed-vac, dissolved in loading buffer (5 μL) and analyzed by denaturing PAGE (20%, 7M urea) and autoradiography. The results are shown in FIG. 10. The lanes in the autoradiogram are numbered and a key is provided above the autoradiogram to indicate the temperature and concentration of KF in each case. Specifically, it is shown that the modified phenols (exemplified by Compounds I and 3-4 above) and naphthols of the invention (exemplified by Compound 2 above) are efficient cross-linkers according to the method of the invention. The dense bands at the bottom of the gel are the $^{32}$P-D$_c$, while the higher bands for each of the agents indicate the alkylated and cross-linked duplex forms created through the silyloxy aromatic compounds of the invention.

Thus, while we have described what are presently the preferred embodiments of the present invention, other and further changes and modifications could be made thereto without departing from the scope of the invention, and it is intended by the inventor herein to claim all such changes and modifications.

We claim:

1. A process for selectively alkylating a target molecule, comprising steps of:

a) providing a probe for recognizing a predetermined binding site on a target molecule;

b) providing a silyloxy aromatic derivative for linking to the probe;

c) linking the probe to the silyloxy aromatic derivative to form a targeted alkylating agent;

d) introducing the targeted alkylating agent to a system containing a target molecule, whereby the probe associates with the target molecule, localizing the linked silyloxy aromatic derivative near the target molecule; and e) activating the targeted alkylating agent, thereby causing covalent binding between the linked aromatic derivative proximal to the association site of the probe with the target molecule.

2. A process as recited in claim 1, wherein the targeted alkylating agent has the molecular formula:

wherein when
$R_1$=—OSiR$_6$R$_7$R$_8$, then $R_2$ and/or $R_4$ is=—CR$_9$R$_{10}$X;
when
$R_2$=—OSiR$_6$R$_7$R$_8$, then $R_1$, $R_3$ and/or $R_5$ is=—CR$_9$R$_{10}$X;
when
$R_3$=—OSiR$_6$R$_7$R$_8$, then $R_2$ and/or $R_4$ is=—CR$_9$R$_{10}$X;
when
$R_4$=—OSiR$_6$R$_7$R$_8$, then $R_1$, $R_3$ and/or $R_5$ is=—CR$_9$R$_{10}$X;
when
$R_5$=—OSiR$_6$R$_7$R$_8$, then $R_2$ and/or $R_4$ is=—CR$_9$R$_{10}$X;
wherein the remaining $R_{1-5}$ not defined above are hydrogen,
wherein said $R_6$, $R_7$, $R_8$=various alkyl or aromatic groups; said $R_9$ and $R_{10}$ is H, or an organic group, including an aliphatic or alkyl group; X=leaving group; L is a linking group for attachment to a probe which may be positioned at any carbon atom of the ring; and Pr is a probe for binding to a target molecule.

3. A process as recited in claim 2, wherein said linking step (c) further comprises adapting the silyloxy aromatic derivative by the addition of an acidic linking group suitably modified for linking the silyloxy aromatic derivative to the probe molecule.

4. A process as recited in claim 3, wherein said probe is an oligonucleotide, and further comprising the step of:
suitably modifying a base of said oligonucleotide probe for linking to L at the modified base.

5. A process as recited in claim 3, wherein said probe is an oligonucleotide, and further comprising the step of:
suitably modifying a phosphoribose backbone of said oligonucleotide probe for linking to L at the modified phosphoribose backbone.

6. A process as recited in claim 3, wherein said activating step comprises introduction of an ionic activating signal.

7. A process as recited in claim 3, wherein said adapting step further includes brominating the X group, and said activating step comprises activation with an ionic signal.

8. A process recited in claim 7, wherein said brominating step is followed by substituting the bromine by molecules selected from the group consisting of Cl, F, I, —OCOR, OH, —OSO$_2$CH$_3$, —OSO$_2$C$_6$H$_4$CH$_3$—p, —OR, —OCONHR, —OCONHCH$_2$CH$_2$R, Br, —OC$_6$H$_5$, —OC$_6$H$_4$NO$_2$, and —SC$_6$H$_5$.

9. A process as recited in claim 7, wherein said process is carried out in vivo, and said process further comprises suitably modifying said probe for traversing a cell membrane of an organism containing said target molecule; and wherein said activating step is achieved by the natural level of ions adjacent to said target molecule.

10. A process as recited in claim 8, wherein L comprises a chain —R$_{11}$—R$_{12}$—R$_{13}$—, in which R$_{11}$ is selected from the group consisting of NH, S, O and CH$_2$, in which R$_{12}$ comprises a stable spacer group between R$_{11}$ and R$_{13}$, and in which R$_{13}$ is selected from the group consisting of —NH$_2$, —SH, —OH and —COOH; and
wherein Pr is a probe that includes a localizing moiety, including an oligonucleotide, protein, intercalating moiety, or other molecule that preferentially localizes to an organic molecule including DNA, RNA, or protein.

11. A process as recited in claim 8, wherein said process is carried out in vitro.

12. A silyloxy aromatic compound, comprising a substituted aromatic ring system, wherein a position on the aromatic ring system is occupied by an —$OSiR_6R_7R_8$ group and at least one position on the aromatic ring system in conjugation with the —$OSiR_6R_7R_8$ group is occupied by a —$CR_9R_{10}X$ group, in which $R_6$, $R_7$, and $R_8$ are selected from the group consisting of alkyl and aromatic groups;

$R_9$ and $R_{10}$ are selected from the group consisting of —H, alkyl, and aromatic groups; and X is a leaving group.

13. The silyloxy aromatic compound of claim 12, wherein two positions on the aromatic ring system in conjugation with the —$OSiR_6R_7R_8$ group are occupied by —$CR_9R_{10}$ X groups.

14. The silyloxy aromatic compound of claim 12, wherein a heteroatom is present within the aromatic ring system without destroying the conjugation between the —$OSiR_6R_7R_8$ and —$CR_9R_{10}$ X groups.

15. The silyloxy aromatic compound of claim 14, wherein said heteroatom is selected from the group consisting of O and N.

16. The silyloxy aromatic compound of claim 12, wherein the aromatic ring system is selected from the group consisting of benzene, naphthalene, anthracene, phenanthrene, quinolines, azanthracenes, and azaphenanthrenes.

17. The silyloxy aromatic compound according to claim 12, wherein said $R_6$ and $R_7$ comprise methyl groups and $R_8$ comprises a t-butyl moiety.

18. The silyloxy aromatic compound according to claim 12, wherein —X is selected from the group consisting of F, Cl, Br, I, —OCOR, OH, —$OSO_2CH_3$, —$OSO_2C_6H_4CH_3$—p, —OR, —OCONHR, —$OCONHCH_2CH_2R$, —$OC_6H_5$, —$OC_6H_4NO_2$, and —$SC_6H_5$.

19. The silyloxy aromatic compound according to claim 18, wherein X is selected from the group consisting of $OC_6H_4NO_2$ and Br.

20. The silyloxy aromatic compound according to claim 12, wherein the silyloxy aromatic compound alkylates a target molecule in response to ionic activation.

21. The silyloxy aromatic compound according to claim 12, wherein a position on the aromatic ring system is occupied by a -L-Pr group, in which L is a linking group for attachment of the aromatic ring system to a probe; and Pr is a probe for binding to a target molecule.

22. The silyloxy aromatic compound according to claim 21, wherein L comprises a chain —$R_{11},R_{12}$—$R_{13}$, in which $R_{11}$ is selected from the group consisting of NH, S, O, and $CH_2$;

$R_{12}$ comprises a stable spacer group between $R_{11}$ and $R_{13}$; and $R_{13}$ is selected from the group consisting of —$NH_2$, —SH, —OH, and —COOH.

23. The silyloxy aromatic compound according to claim 21, wherein Pr is a probe that includes a localizing moiety.

24. The silyloxy aromatic compound according to claim 23, wherein the localizing moiety non-specifically localizes to a target molecule.

25. The silyloxy aromatic compound according to claim 23, wherein the localizing moiety specifically localizes to a target molecule.

26. The silyloxy aromatic compound according to claim 23, wherein the localizing moiety includes oligonucleotide, protein, intercalator, or other molecule that localizes to an organic target molecule including DNA, RNA, or protein.

27. The silyloxy aromatic compound according to claim 26, wherein the localizing moiety is an oligonucleotide.

28. The silyloxy aromatic compound according to claim 26, wherein the localizing moiety is a protein.

29. The silyloxy aromatic compound according to claim 26, wherein the localizing moiety is a DNA strand.

30. The silyloxy aromatic compound according to claim 26, wherein the localizing moiety is an intercalator.

* * * * *